US012611543B2

(12) United States Patent
Yoder et al.

(10) Patent No.: US 12,611,543 B2
(45) Date of Patent: *Apr. 28, 2026

(54) TELEMETRY OVERUSE REDUCTION IN A MEDICAL DEVICE

(71) Applicant: Medtronic, Inc., Minneapolis, MN (US)

(72) Inventors: Matthew R. Yoder, Franklin, WI (US); Bo Zhang, Blaine, MN (US); Gary P. Kivi, Maple Grove, MN (US); Richard A. Sanden, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 22 days.

This patent is subject to a terminal disclaimer.

(21) Appl. No.: 18/421,505

(22) Filed: Jan. 24, 2024

(65) Prior Publication Data

US 2024/0238600 A1 Jul. 18, 2024

Related U.S. Application Data

(63) Continuation of application No. 17/157,314, filed on Jan. 25, 2021, now Pat. No. 11,904,173, which is a
(Continued)

(51) Int. Cl.
*A61N 1/372* (2006.01)
*G16H 40/63* (2018.01)

(52) U.S. Cl.
CPC ..... *A61N 1/37252* (2013.01); *A61N 1/37217* (2013.01); *A61N 1/37254* (2017.08); *A61N 1/37276* (2013.01); *G16H 40/63* (2018.01)

(58) Field of Classification Search
CPC ............ A61N 1/37217; A61N 1/37254; A61N 1/37276
See application file for complete search history.

(56) References Cited

U.S. PATENT DOCUMENTS

| | | | |
|---|---|---|---|
| 8,229,562 B2 | 7/2012 | Ginggen et al. | |
| 8,386,051 B2 | 2/2013 | Rys | |

(Continued)

FOREIGN PATENT DOCUMENTS

WO 2007070794 A2 6/2007

OTHER PUBLICATIONS (PCT/US2017/013719) PCT Notification of Transmittal of the International Search Report and the Written Opinion of the International Searching Authority, Mailed Mar. 24, 2017, 13 pages.
(Continued)

*Primary Examiner* — Joseph M Dietrich
(74) *Attorney, Agent, or Firm* — Shumaker & Sieffert, P.A.

(57) ABSTRACT

Systems, apparatus, methods and computer-readable storage media facilitating telemetry overuse reduction in a medical device, such as an implantable medical device ("IMD") are provided. In one embodiment, an IMD includes a housing configured to be implanted at least partially within a patient, a memory and circuitry within the housing and a processor that executes executable components stored in the memory. The executable components include: a communication component configured to establish a telemetry connection with an external device to communicate data associated with sensed physiological data or therapy; and an authorization component configured to determine whether the external device is authorized to communicate with the IMD, wherein the communication component is further configured to disable the telemetry connection with the external device and prevent additional communication with the external device for a defined period of time based on a determination that the external device fails to be authorized to communicate with the IMD.

20 Claims, 12 Drawing Sheets

Related U.S. Application Data continuation of application No. 16/273,241, filed on Feb. 12, 2019, now Pat. No. 10,898,721, which is a continuation of application No. 15/009,505, filed on Jan. 28, 2016, now Pat. No. 10,201,712.

(56) References Cited

U.S. PATENT DOCUMENTS

| | | | |
|---|---|---|---|
| 8,475,372 | B2 | 7/2013 | Schell et al. |
| 8,626,144 | B2 | 1/2014 | Talty et al. |
| 8,913,748 | B2 | 12/2014 | Ho et al. |
| 9,072,914 | B2 | 7/2015 | Greenhut et al. |
| 9,687,658 | B2 | 6/2017 | Wu et al. |
| 9,855,433 | B2 | 1/2018 | Shahandeh et al. |
| 10,201,712 | B2 * | 2/2019 | Yoder ............... A61N 1/37252 |
| 10,898,721 | B2 * | 1/2021 | Yoder ................... G16H 40/63 |
| 11,904,173 | B2 * | 2/2024 | Yoder ............... A61N 1/37254 |
| 2003/0149459 | A1 | 8/2003 | VonArx et al. |
| 2009/0270949 | A1 | 10/2009 | Kalpin et al. |
| 2011/0015693 | A1 | 1/2011 | Williamson |
| 2012/0108922 | A1 | 5/2012 | Schell et al. |
| 2012/0166680 | A1 | 6/2012 | Masoud et al. |
| 2012/0172690 | A1 | 7/2012 | Anderson et al. |
| 2012/0172941 | A1 | 7/2012 | Rys |
| 2012/0271380 | A1 | 10/2012 | Roberts et al. |
| 2013/0214909 | A1 | 8/2013 | Meijers et al. |
| 2013/0259230 | A1 | 10/2013 | Polo et al. |
| 2014/0188348 | A1 | 7/2014 | Gautama et al. |
| 2014/0214104 | A1 | 7/2014 | Greenhut et al. |
| 2014/0330327 | A1 | 11/2014 | Thompson-Nauman et al. |
| 2015/0049871 | A1 | 2/2015 | Xie et al. |
| 2015/0073500 | A1 | 3/2015 | Kothandaraman et al. |
| 2015/0133951 | A1 | 5/2015 | Seifert et al. |
| 2015/0341785 | A1 | 11/2015 | Young et al. |
| 2016/0250486 | A1 | 9/2016 | Yoder et al. |
| 2016/0250490 | A1 | 9/2016 | Hoffman et al. |
| 2017/0026777 | A1 | 1/2017 | Denboer et al. |
| 2021/0146145 | A1 | 5/2021 | Yoder et al. |

OTHER PUBLICATIONS

Prosecution History from U.S. Appl. No. 15/009,505, now U.S. Pat. No. 10,201,712, dated Jun. 30, 2017 through Oct. 2, 2018, 48 pp.
Prosecution History from U.S. Appl. No. 16/273,241, now U.S. Pat. No. 10,898,721, dated Jun. 15, 2020 through Oct. 7, 2020, 16 pp.
Prosecution History from U.S. Appl. No. 17/157,314, dated May 25, 2021 through Dec. 18, 2023, 48 pp.

* cited by examiner

100

102

108
104
106

110b
110a 112a
112b
114a
114b

EXTERNAL
DEVICE
116

Telemetry Regulation for 24 Hour Period

| | Device ID | Authentication failure type | Time | Data usage total |
|---|---|---|---|---|
| 1 | 775632 | 1 | 10:12 | 25KB |
| 2 | 468965 | 4 | 11:32 | 30KB |
| 3 | 775632 | 1 | 12:21 | 32KB |
| 4 | 674978 | 3 | 13:01 | 36KB |
| 5 | 346521 | 2 | 16:45 | 58KB |
| 6 | 567991 | 1 | 17:08 | 60KB |
| 7 | 456377 | 4 | 19:33 | 71KB |
| 8 | 349371 | 4 | 21:40 | 79KB |
| 9 | 459987 | 5 | 22:50 | 83KB |
| 10 | 459987 | 5 | 22:55 | 84KB |

FIG. 3A

Telemetry Regulation for 24 Hour Period

| | Device ID | Authentication failure type | Time | Data usage total |
|---|---|---|---|---|
| 1 | 775632 | 1 | 10:12 | 25KB |
| 2 | 468965 | 4 | 11:32 | 30KB |
| 3 | 775632 | 1 | 12:21 | 32KB |
| 4 | 674978 | 3 | 13:01 | 36KB |
| 5 | 346521 | 2 | 16:45 | 58KB |
| 6 | 775632 | 1 | 17:08 | 60KB |
| *Maximum unauthorized attempts reached - Disable telemetry - 17:09 - 24:00* | | | | |

FIG. 3B

List of Unauthorized Devices

| | Device ID |
|---|---|
| 1 | 899778 |
| 2 | 112388 |
| 3 | 444981 |
| 4 | 632751 |
| 5 | 775632 |

FIG. 3C

Telemetry Regulation for 24 Hour Period

| | Device ID | Authentication failure type | Time | Data usage total | Regulation Score |
|---|---|---|---|---|---|
| 1 | 775632 | 1 | 10:12 | 25KB | 11% |
| 2 | 468965 | 4 | 11:32 | 30KB | 18% |
| 3 | 775632 | 1 | 12:21 | 32KB | 21% |
| 4 | 674978 | 3 | 13:01 | 36KB | 25% |
| 5 | 346521 | 2 | 16:45 | 58KB | 27% |
| 6 | 567991 | 1 | 17:08 | 60KB | 33% |
| 7 | 456377 | 4 | 19:33 | 71KB | 40% |
| 8 | 349371 | 4 | 21:40 | 79KB | 44% |
| 9 | 459987 | 5 | 22:50 | 83KB | 49% |
| 10 | 459987 | 5 | 22:55 | 84KB | 56% |

Regulation score > 50% - Disable telemetry - 22:55 - 24:00

FIG. 4

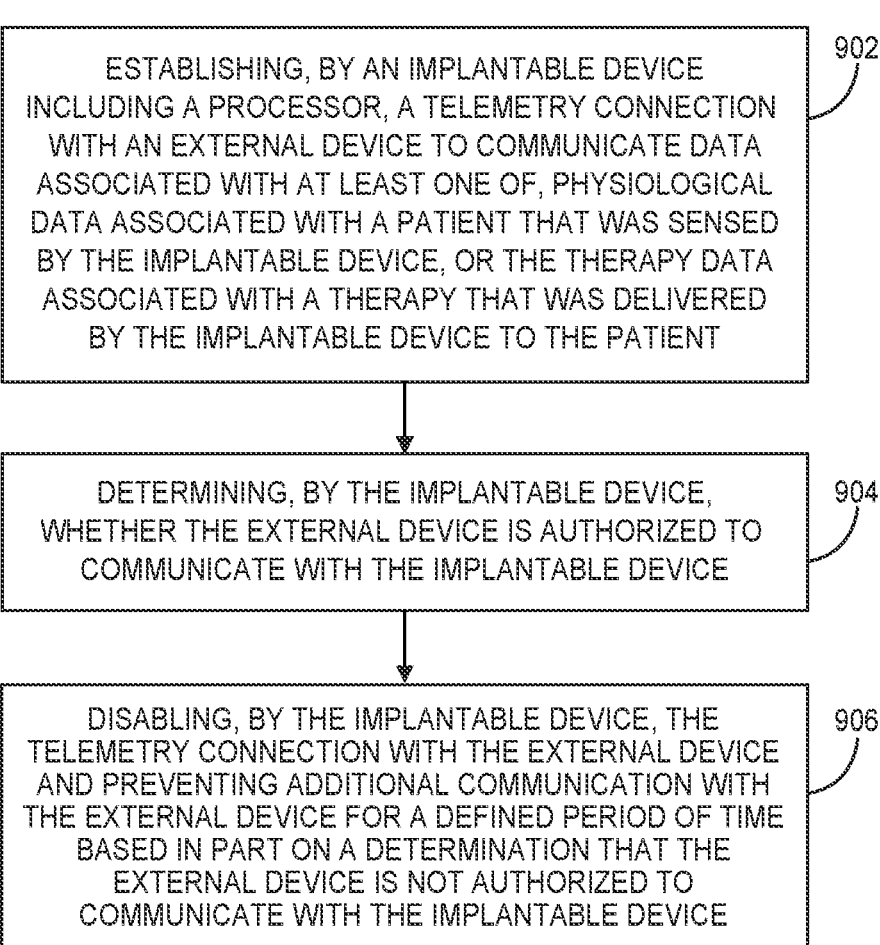

900

ESTABLISHING, BY AN IMPLANTABLE DEVICE INCLUDING A PROCESSOR, A TELEMETRY CONNECTION WITH AN EXTERNAL DEVICE TO COMMUNICATE DATA ASSOCIATED WITH AT LEAST ONE OF, PHYSIOLOGICAL DATA ASSOCIATED WITH A PATIENT THAT WAS SENSED BY THE IMPLANTABLE DEVICE, OR THE THERAPY DATA ASSOCIATED WITH A THERAPY THAT WAS DELIVERED BY THE IMPLANTABLE DEVICE TO THE PATIENT — 902

DETERMINING, BY THE IMPLANTABLE DEVICE, WHETHER THE EXTERNAL DEVICE IS AUTHORIZED TO COMMUNICATE WITH THE IMPLANTABLE DEVICE — 904

DISABLING, BY THE IMPLANTABLE DEVICE, THE TELEMETRY CONNECTION WITH THE EXTERNAL DEVICE AND PREVENTING ADDITIONAL COMMUNICATION WITH THE EXTERNAL DEVICE FOR A DEFINED PERIOD OF TIME BASED IN PART ON A DETERMINATION THAT THE EXTERNAL DEVICE IS NOT AUTHORIZED TO COMMUNICATE WITH THE IMPLANTABLE DEVICE — 906

FIG. 9

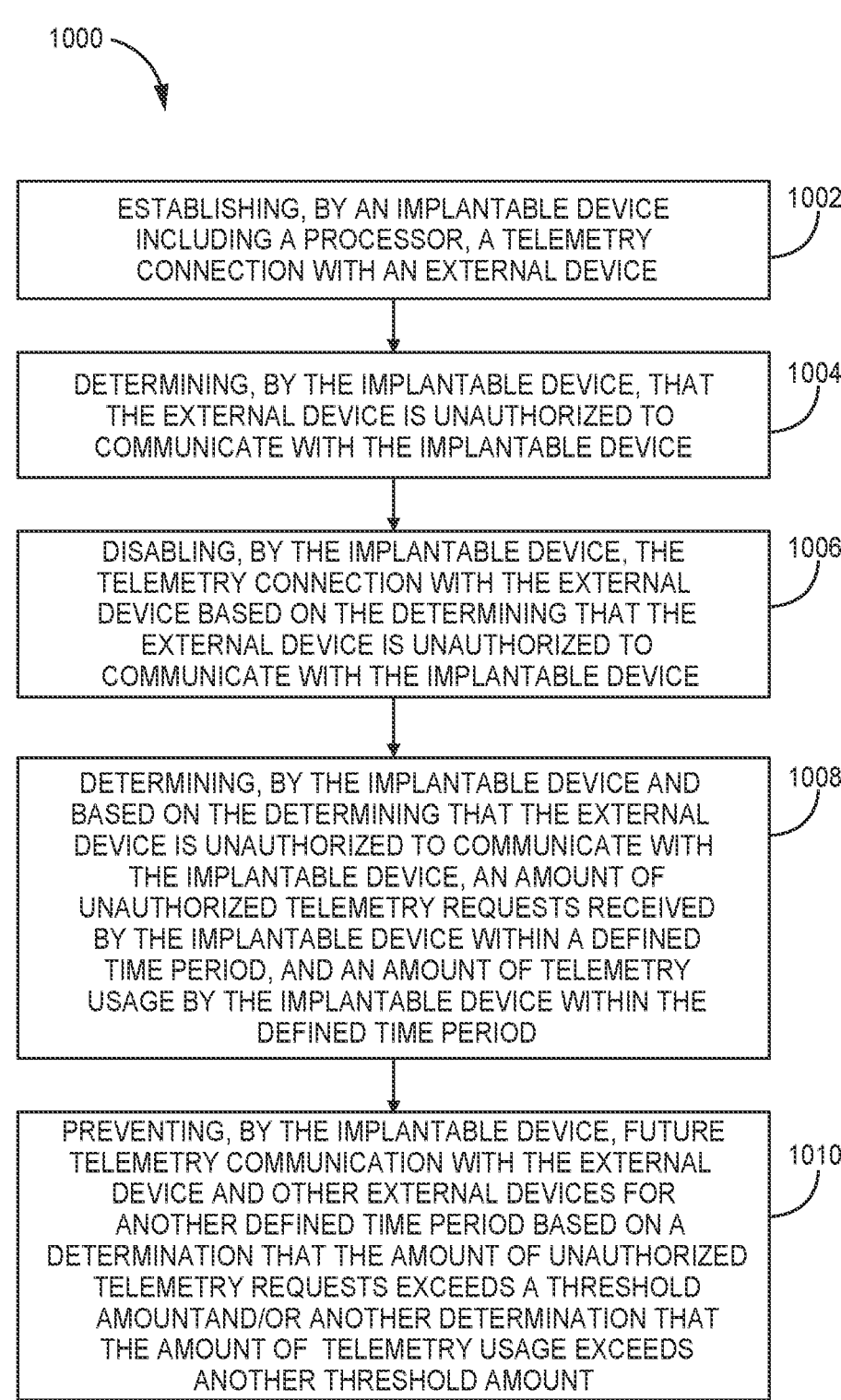

1000

ESTABLISHING, BY AN IMPLANTABLE DEVICE INCLUDING A PROCESSOR, A TELEMETRY CONNECTION WITH AN EXTERNAL DEVICE — 1002

DETERMINING, BY THE IMPLANTABLE DEVICE, THAT THE EXTERNAL DEVICE IS UNAUTHORIZED TO COMMUNICATE WITH THE IMPLANTABLE DEVICE — 1004

DISABLING, BY THE IMPLANTABLE DEVICE, THE TELEMETRY CONNECTION WITH THE EXTERNAL DEVICE BASED ON THE DETERMINING THAT THE EXTERNAL DEVICE IS UNAUTHORIZED TO COMMUNICATE WITH THE IMPLANTABLE DEVICE — 1006

DETERMINING, BY THE IMPLANTABLE DEVICE AND BASED ON THE DETERMINING THAT THE EXTERNAL DEVICE IS UNAUTHORIZED TO COMMUNICATE WITH THE IMPLANTABLE DEVICE, AN AMOUNT OF UNAUTHORIZED TELEMETRY REQUESTS RECEIVED BY THE IMPLANTABLE DEVICE WITHIN A DEFINED TIME PERIOD, AND AN AMOUNT OF TELEMETRY USAGE BY THE IMPLANTABLE DEVICE WITHIN THE DEFINED TIME PERIOD — 1008

PREVENTING, BY THE IMPLANTABLE DEVICE, FUTURE TELEMETRY COMMUNICATION WITH THE EXTERNAL DEVICE AND OTHER EXTERNAL DEVICES FOR ANOTHER DEFINED TIME PERIOD BASED ON A DETERMINATION THAT THE AMOUNT OF UNAUTHORIZED TELEMETRY REQUESTS EXCEEDS A THRESHOLD AMOUNTAND/OR ANOTHER DETERMINATION THAT THE AMOUNT OF TELEMETRY USAGE EXCEEDS ANOTHER THRESHOLD AMOUNT — 1010

FIG. 10

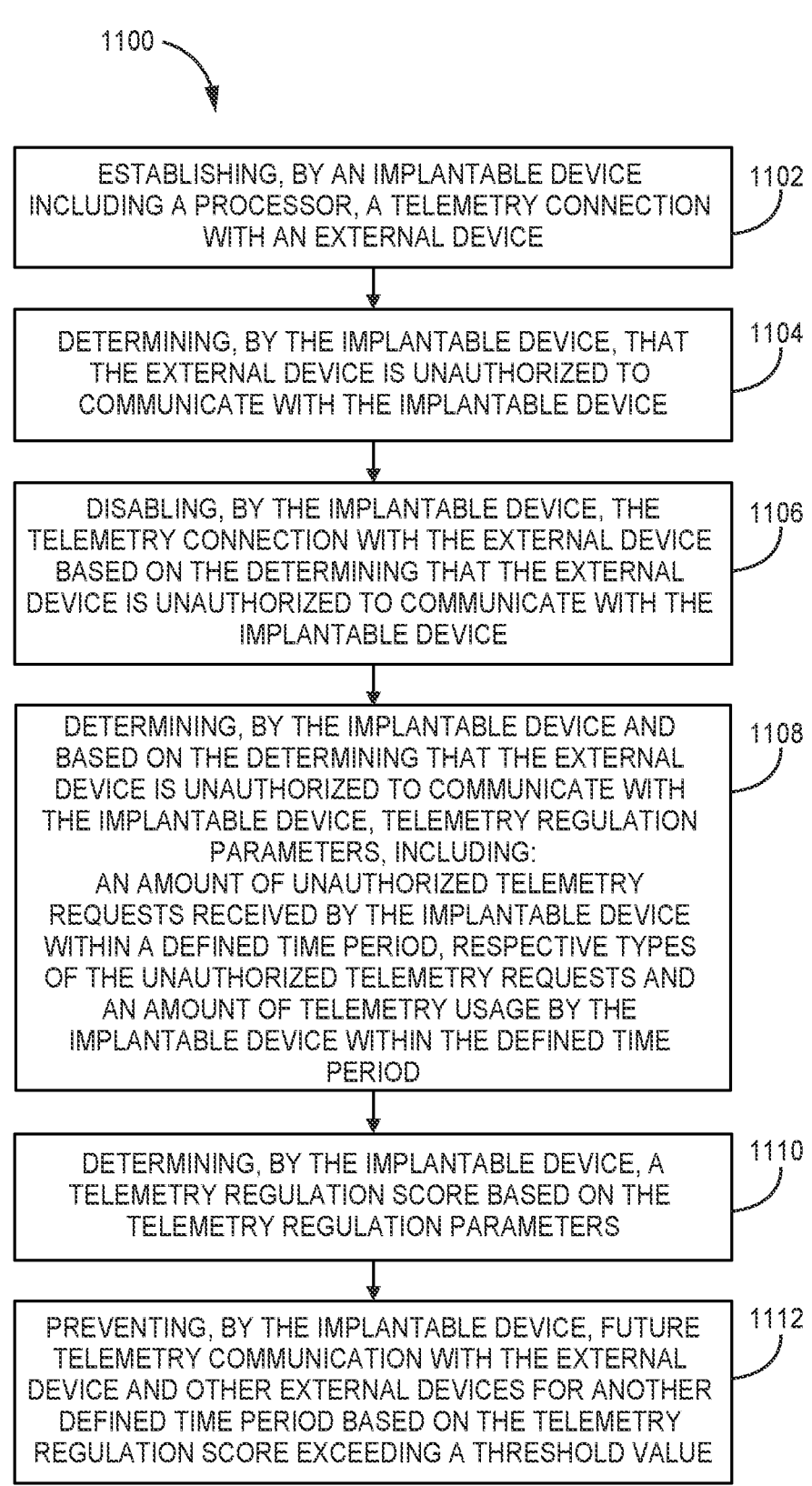

1100

ESTABLISHING, BY AN IMPLANTABLE DEVICE INCLUDING A PROCESSOR, A TELEMETRY CONNECTION WITH AN EXTERNAL DEVICE — 1102

DETERMINING, BY THE IMPLANTABLE DEVICE, THAT THE EXTERNAL DEVICE IS UNAUTHORIZED TO COMMUNICATE WITH THE IMPLANTABLE DEVICE — 1104

DISABLING, BY THE IMPLANTABLE DEVICE, THE TELEMETRY CONNECTION WITH THE EXTERNAL DEVICE BASED ON THE DETERMINING THAT THE EXTERNAL DEVICE IS UNAUTHORIZED TO COMMUNICATE WITH THE IMPLANTABLE DEVICE — 1106

DETERMINING, BY THE IMPLANTABLE DEVICE AND BASED ON THE DETERMINING THAT THE EXTERNAL DEVICE IS UNAUTHORIZED TO COMMUNICATE WITH THE IMPLANTABLE DEVICE, TELEMETRY REGULATION PARAMETERS, INCLUDING:
AN AMOUNT OF UNAUTHORIZED TELEMETRY REQUESTS RECEIVED BY THE IMPLANTABLE DEVICE WITHIN A DEFINED TIME PERIOD, RESPECTIVE TYPES OF THE UNAUTHORIZED TELEMETRY REQUESTS AND AN AMOUNT OF TELEMETRY USAGE BY THE IMPLANTABLE DEVICE WITHIN THE DEFINED TIME PERIOD — 1108

DETERMINING, BY THE IMPLANTABLE DEVICE, A TELEMETRY REGULATION SCORE BASED ON THE TELEMETRY REGULATION PARAMETERS — 1110

PREVENTING, BY THE IMPLANTABLE DEVICE, FUTURE TELEMETRY COMMUNICATION WITH THE EXTERNAL DEVICE AND OTHER EXTERNAL DEVICES FOR ANOTHER DEFINED TIME PERIOD BASED ON THE TELEMETRY REGULATION SCORE EXCEEDING A THRESHOLD VALUE — 1112

FIG. 11

TELEMETRY OVERUSE REDUCTION IN A MEDICAL DEVICE

CROSS REFERENCE TO RELATED APPLICATIONS

This application is a continuation of U.S. patent application Ser. No. 17/157,314 filed Jan. 25, 2021, which is a continuation of U.S. patent application Ser. No. 16/273,241 (now U.S. Pat. No. 10,898,721), filed Feb. 12, 2019, which is a continuation of and claims the benefit of and priority to U.S. patent application Ser. No. 15/009,505 (now U.S. Pat. No. 10,201,712), filed Jan. 28, 2016, the content of each which are incorporated herein by reference in their entirety.

TECHNICAL FIELD

This disclosure relates generally to medical devices and, more particularly, to devices, systems, apparatus, methods and computer-readable storage media facilitating telemetry overuse reduction in a medical device, such as implantable device.

BACKGROUND

Modern healthcare facilitates the ability for patients to lead healthy and full lives. Implantable medical devices (IMDs) are often utilized for such medical advances. For example, IMDs such as pacemakers, implantable cardio-verter-defibrillators (ICDs), neurostimulators, and drug pumps can facilitate management with a wide range of ailments, including, but not limited to, cardiac arrhythmias, diabetes, and Parkinson's disease. Patients and medical care providers can monitor the IMD and assess a patient's current and historical physiological state to identify and/or predict impending events or conditions.

Implantable devices, including IMDs, are increasing in complexity while shrinking in size. One hurdle to achieving such small and highly functional devices is efficient power management. In particular, many implantable devices oper-ate from power sources that have a limited lifespan and/or are not rechargeable. As such, after the implantable device is implanted within the human body and the lifespan of the power source has been reached, the implantable device may need to be removed.

Telemetry communication performed between an implantable device and an external device can have a significant impact on the lifespan of the power source of an implantable device. As commercially available telemetry protocols grow in use, the knowledge of how to initiate a telemetry session with an implantable device can become publicly available. Corresponding scenarios can occur in which unauthorized third party devices may initiate a telem-etry session with an implantable device in an effort to prematurely deplete the battery of the implantable device. Thus, systems, apparatus, methods and computer-readable storage media that minimize or prevent telemetry overuse of implantable devices via communication with unauthorized devices are desired.

SUMMARY

The following presents a simplified summary of one or more of the embodiments in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description can include additional or alternative embodi-ments beyond those described in the Summary section.

Embodiments described herein include devices, systems, apparatus, methods and computer-readable storage media that facilitate telemetry overuse reduction in a medical device. In some embodiments, the medical device is or includes an implantable medical device (IMD). In other embodiments, the medical device is or includes a device configured to interact with the IMD. In these embodiments, both the implantable device and the IMD can be implanted within a patient.

In one embodiment, an IMD is provided. The IMD is configured to be at least partially implanted within a patient and includes a housing configured to be implanted at least partially within the patient, a memory, within the housing, that stores executable components, and circuitry, within the housing, and configured to at least one of obtain sensed physiological data associated with the patient or deliver a therapy to the patient. The IMD also includes a processor, within the housing, that executes the executable components stored in the memory. The executable components include at least a communication component configured to establish a telemetry connection with an external device, and an autho-rization component configured to determine whether the external device is authorized to communicate with the IMD. In some embodiments, the communication component is further configured to disable the telemetry connection with the external device and prevent additional communication with the external device for a defined period of time based on a determination that the external device fails to be authorized to communicate with the IMD. The defined period of time can be a static period of time or a period of time that can change from time to time based on configu-ration or programming of the IMD, or based on one or more different factors. In other embodiments, the communication component is configured to disable the telemetry connection with the external device and prevent additional communi-cation with the external device and other external devices for the defined period of time based on the determination that the external device fails to be authorized to communicate with the IMD.

In some implementations, the communication component is configured to establish the telemetry connection with the external device using the Bluetooth Low Energy (BLE) communication protocol.

For example, the authorization component can determine whether the external device is authorized to communicate with the IMD based on reception of valid authorization information from the external device. In another example, the authorization component can determine whether the external device is authorized to communicate with the IMD based on reception of a defined packet from the external device within a defined window of time following reception of a request, from the external device, to establish the telemetry connection. In yet another example, the authori-zation component can determine whether the external device is authorized to communicate with the IMD based on reception of a defined packet from the external device within a defined window of time following transmission of an acknowledgment message to the external device by the IMD, wherein the acknowledgment message indicates the IMD has received a request, from the external device, to establish the telemetry connection.

In some embodiments, the IMD can also include a telemetry regulation component configured to determine, based on a determination that the external device fails to be authorized to communicate with the IMD, a number of previous failed attempts to authorize the external device in association with establishing a telemetry connection with the IMD.

In some embodiments, the communication component is further configured to disable the telemetry connection with the external device and prevent additional communication with the external device for the defined period of time based on the determination that the external device fails to be authorized to communicate with the implantable device and a determination that the number of previous failed attempts exceeds a threshold amount.

In another implementation, based on the determination that the external device fails to be authorized to communicate with the implantable device and a determination that the number of previous failed attempts exceeds the threshold amount, the telemetry regulation component is further configured to determine an amount of telemetry communication conducted by the implantable device over another defined period of time. According to this implementation, the communication component is further configured to disable the telemetry connection with the external device and enable additional telemetry communication with the external device and the other external devices based on a determination that the amount of telemetry communication fails to exceed the threshold. However, the communication component is configured to disable the telemetry connection with the external device and prevent additional telemetry communication with the external device and other external devices based on a determination that the amount of telemetry communication exceeds the threshold.

In another embodiment, a method of communicating by an implantable medical device configured to at least one of obtain sensed physiological data associated with a patient or deliver a therapy to the patient, is provided. The method can include receiving, by the implantable medical device including a processor, a request from an external device to establish a telemetry session between the external device and the implantable medical device. The method also includes determining whether the external device is authorized to establish the telemetry session with the implantable medical device. The method also includes deactivating a receiver of the implantable medical device for a defined period of time based on a determination that the external device fails to be authorized to establish the telemetry session with the implantable medical device.

The method can employ various techniques to determine whether the external device is authorized to establish the telemetry session with the implantable medical device. For example, the determining whether the external device is authorized to establish the telemetry session with the implantable medical device can be based on reception of valid authorization information from the external device and/or based on reception of a defined packet from the external device within a defined window of time following the request.

In some embodiments, the method can also include, based on a determination that the external device fails to be authorized to communicate with the implantable medical device, determining a number of previous failed attempts to authorize the external device in association with establishing a telemetry session with the implantable medical device. In some implementations, the deactivating is further based on a determination that the number of previous failed attempts exceeds a threshold amount. In another implementation, the method can also include, based on the determination that the external device fails to be authorized to communicate with the implantable medical device, and a determination that the number of previous failed attempts exceeds the threshold amount, determining an amount of telemetry communication conducted by the implantable medical device over another defined period of time. According to this implementation, the deactivating is further based on a determination that the amount of telemetry communication exceeds another threshold amount.

In various additional embodiments, a system includes a remote device configured to perform telemetry communications with other devices and an implantable device. The implantable device is configured to establish an unsecure telemetry connection with the remote device based on reception of a request from the remote device to communicate with the implantable device. The implantable device is further configured to determine whether the remote device is authorized to establish a secure telemetry connection with the implantable device, and disable the unsecure telemetry connection with the external device and prevent additional telemetry communication with the external device and other external devices for a defined period of time, based in part on a determination that the external device is not authorized to establish the secure telemetry connection with the implantable device.

In some implementations, the implantable device is further configured to prevent the additional telemetry communication with the external device and the other external devices based on an amount of telemetry requests received from unauthorized devices in the another defined period and an amount of telemetry communication performed by the implantable device in the other defined period of time. The remote device can include a mobile phone, a tablet, or other suitable computing device.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification can be employed. Other advantages and novel features of the embodiments described will become apparent from the following detailed description of the specification when considered in conjunction with the drawings.

BRIEF DESCRIPTION OF THE DRAWINGS

FIG. 3A illustrates an example, non-limiting table including telemetry regulation information monitored over a period of time by an implantable device and not resulting in disabled telemetry performance in accordance with one or more embodiments described herein.

FIG. 3B illustrates an example, non-limiting table including telemetry regulation information monitored over a period of time by an implantable device and resulting in disabled telemetry performance to facilitate telemetry over-use reduction in accordance with one or more embodiments described herein.

FIG. 3C illustrates example, non-limiting stored information identifying devices associated with a list of unauthorized devices with which the implantable device will not communicate in accordance with one or more embodiments.

FIG. 4 illustrates an example, non-limiting table including telemetry regulation information monitored over a period of time by an implantable device and resulting in disabled telemetry performance to facilitate telemetry overuse reduction in accordance with one or more embodiments described herein.

FIGS. 5-11 illustrate flow diagrams of example, non-limiting methods that facilitate telemetry overuse reduction in an implantable device in accordance with one or more embodiments described herein.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

Figure 1:
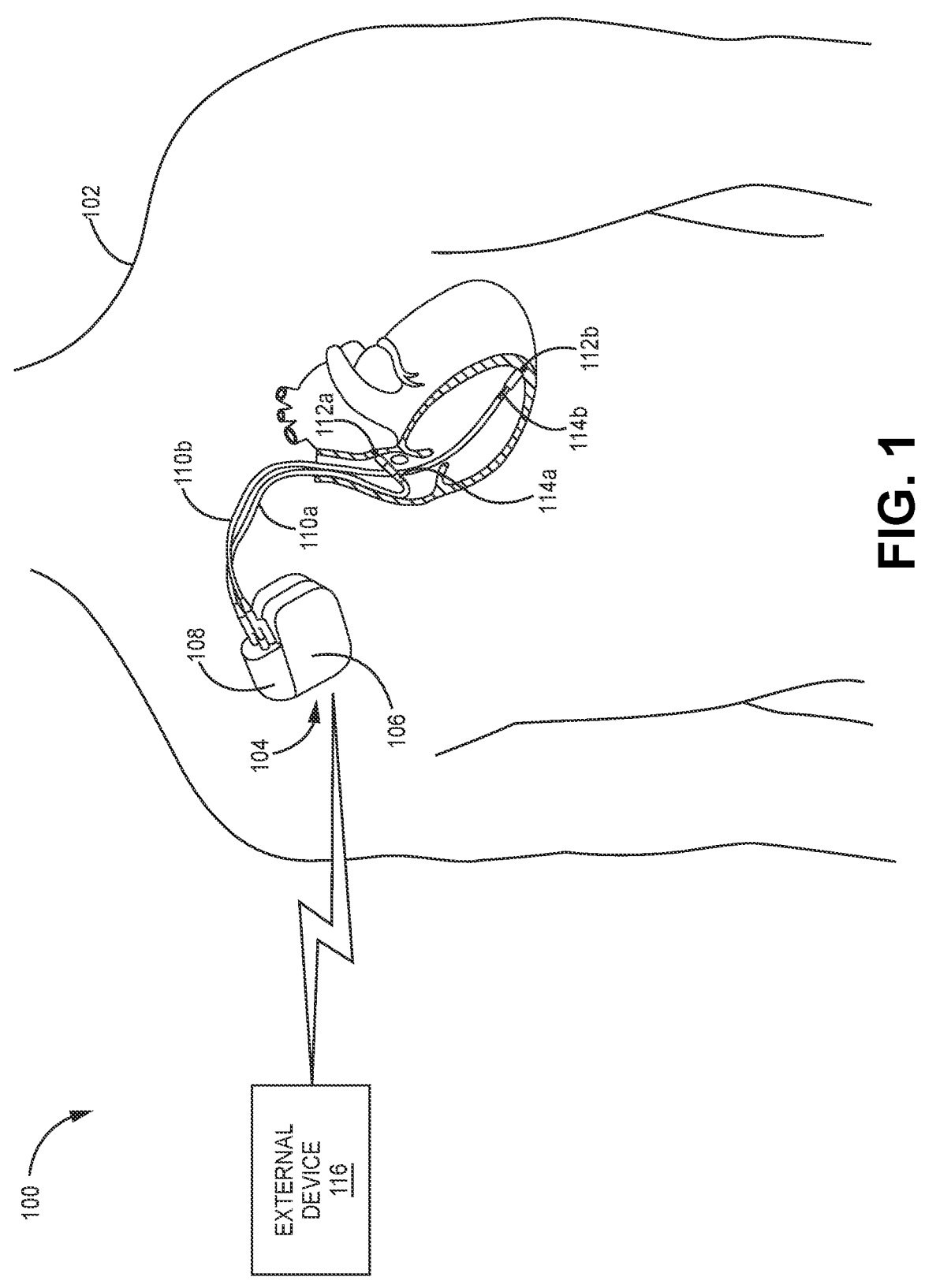
FIG. 1 illustrates a schematic diagram of an example, non-limiting medical device telemetry system configured to facilitate telemetry overuse reduction in an implantable device in accordance with one or more embodiments described herein.

With reference now to the drawings, FIG. 1 illustrates a schematic diagram of an example, non-limiting medical device telemetry system configured to facilitate telemetry overuse reduction in an implantable device in accordance with one or more embodiments described herein. In the embodiment shown, medical device telemetry system 100 includes an implantable device 104 implanted within a body 102, and an external device 116. In some embodiments, the implantable device 104 is an IMD that is also configured to facilitate one or more diagnostic or treatment functions relative to the body 102. In other embodiments, the implantable device 104 is separate from an IMD (not shown in this embodiment) that is also implanted within the body 102 and communicatively and/or electrically coupled to the IMD.

Embodiments of devices, apparatus and systems herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

One or more embodiments of medical device telemetry system 100 are described in connection with minimizing telemetry overuse of the implantable device 104 in association with performing telemetry communication with one or more external devices, such as external device 116. In particular, implantable device 104 can use wireless telemetry to exchange various types of information with external devices, including external device 116. For example, using wireless telemetry, the implantable device 104 can transmit information to the external device 116. The information transmitted can include, but is not limited to, sensed physiological or biometric data from the body 102, diagnostic determinations made based on the sensed physiological or biometric data, therapy data associated with a therapy delivered to the body, and/or performance data regarding operation and performance of the implantable device 104 (e.g., power level information, information regarding strengths of signals received, information regarding frequency of received interrogation requests, remaining battery life, etc.). In some implementations, the implantable device 104 is an IMD configured to sense the physiological data or the biometric data from the body 102. The IMD can also provide therapy to the body 102 and retain the therapy information regarding the therapy that was provided. In other implementations, the implantable device 104 is associated with an implantable medical device configured to sense the physiological or biometric data or provide the therapy to the body 102. Information associated with the implantable device 104 can be provided to a wide variety of external devices, including, but not limited to, a tablet computer associated with a patient or a physician, a smartphone associated with a patient or a physician, a medical device associated with a patient or a physician, an electronic device at a home of a patient or at an office of a physician, an off-the-shelf device purchased at a store, etc.

In another example, the external device 116 can employ telemetry communication to read data captured by the implantable device 104 (e.g., electrogram data or other physiological or biometric data sensed by the implantable device 104). In another example, using wireless telemetry, the external device 116 can send information or signals to the implantable device 104 to program the implantable device 104 or to configure or re-configure the implantable device 104.

In various embodiments, the implantable device 104 and/or the external device 116 can communicate employing proprietary and/or commercially available public communication protocols. By way of example, but not limitation, the communication protocols can include, but are not limited to, BLUETOOTH®, BLUETOOTH® low energy (BLE), near field communication (NFC), Wireless Fidelity (Wi-Fi) protocol, Zigbee®, RF4CE, WirelessHART, 6LoWPAN, Z-Wave, ANT, and the like. There is a desire to use commercially available telemetry communication protocols for wireless communication between implantable devices and external devices (e.g., implantable device 104 and external device 116) in order to more easily facilitate widespread provisioning of telemetry solutions. For example, many modern mobile devices such as smartphones, tablet personal computer (PC), and the like are configured to communicate using various public telemetry protocols.

As commercially available telemetry protocols are more frequently employed to conduct telemetry with an implantable device (e.g., implantable device 104), the knowledge of how to initiate a telemetry session with an implantable device can become publicly available. As a result, an external device (e.g., external device 116) capable of employing the commercially available telemetry protocol (e.g., a smartphone, a tablet PC, and the like) may be able to initiate a telemetry session with an implantable device (e.g., implantable device 104), even if the external device is not authorized to communicate with the implantable device.

For example, according to various commercially available telemetry protocols (e.g., BLE), in order to initiate a telemetry session with an implantable device (e.g., implantable device 104), an external device (e.g., external device 116) can send a connection request to an implantable device (e.g., implantable device 104) requesting to establish a telemetry session with the implantable device. In some applications, the external device can send the request following detection of a beacon or advertising signal that is periodically transmitted by the implantable device 104. For example, the advertising signal can include information identifying the implantable device 104 and indicating the implantable device 104 is ready and available for performing telemetry communication with another device. According to these embodiments, the implantable device 104 can be configured to maintain activation of a receiver of the implantable device 104 for a defined window of time following transmission of the advertisement signal to wait for possible reception of a connection request from an external device.

Upon reception of a connection request from an external device (e.g., external device 116) by the implantable device (e.g., implantable device 104), an initial telemetry connection can be established between the implantable device 104 and the external device 116. The implantable device 104 can then determine whether the external device 116 is authorized to communicate with the implantable device 104. For example, the implantable device 104 and the external device 116 can begin a process that facilitates establishing a secure or trusted telemetry session between the implantable device 104 and the external device 116, generally referred to as a pairing process. In accordance with various commercially available telemetry protocols, during the pairing process the external device 116 can provide the implantable device 104 with downlink information indicating communication parameters for the telemetry session. In some implementations, this information received at the implantable device 104 can also include authentication information for the external device 116 (e.g., a cryptographic key, a device identifier, a message authentication code (MAC), etc.).

In some embodiments, the implantable device 104 can also analyze and process the information received from the external device 116 to determine whether the external device 116 is authorized to communicate with the implantable device 104. If the information received at the implantable device 104 is not received within a defined window of time or if the information received at the implantable device 104 is invalid (e.g., due to invalid communication parameters, invalid authentication information, etc.), the implantable device 104 can terminate the initial telemetry connection. Nevertheless, although the telemetry connection with the unauthorized external device is terminated, the implantable device 104 has used battery power to establish the initial connection with the external device 116 and to perform the pairing/authentication process. Accordingly, unauthorized external devices (e.g., external device 116) can initiate the process of establishing a telemetry session with implantable device 104, thereby causing the implantable device 104 to unnecessarily use battery power to establish the telemetry session and perform the pairing/authentication process.

In accordance with various embodiments, system 100 can facilitate extension of the lifespan of a power source of implantable device 104 by minimizing or preventing the occurrence of intentional battery drainage communications from unauthorized devices. The disclosed techniques can also be used to regulate an amount of telemetry conducted by the implantable device 104 with authorized devices to minimize or prevent battery overuse by the implantable device 104.

In various embodiments, following reception, by implantable device 104, of a connection request from an external device 116, the implantable device 104 is configured to establish an unsecure telemetry connection with the external device 116 and determine whether the external device 116 is authorized to communicate with the implantable device 104.

In some embodiments, the implantable device 104 employs a pairing process to establish the secure telemetry session between the implantable device 104 and the external device 116. In accordance with the pairing process, the implantable device 104 determines whether the external device 116 is authorized to communicate with the implantable device 104. In response to a determination that the external device 116 is unauthorized to communicate with the implantable device 104, the implantable device 104 can disable the current unsecure telemetry connection with the unauthorized external device 116.

Each time (or, in some embodiments, one or more times) that the implantable device 104 determines that an external device (e.g., external device 116) requesting to establish a telemetry session is unauthorized to communicate with the implantable device 104, the implantable device 104 can perform a telemetry regulation procedure. The telemetry regulation procedure can be a procedure designed to minimize or prevent the occurrence of intentional battery drainage communications from unauthorized external devices, as well as regulate an amount of telemetry conducted by the implantable device 104 with authorized devices to minimize or prevent battery overuse.

In some embodiments, the telemetry regulation procedure can track and/or analyze information including, but not limited to, a number of unauthorized telemetry requests received from a particular external device (e.g., external device 116) within a defined period of time (e.g., a twenty four hour period), a frequency of unauthorized telemetry requests received from a particular external device (e.g., external device 116) within a defined window of time (e.g., five minutes, ten minutes, one hour, five hours, etc.), a number of unauthorized telemetry requests received by the implantable device 104 from any of one or more external devices within a defined period of time, and/or a frequency of unauthorized telemetry requests received by the implantable device 104 from any of one or more external devices within a defined window of time.

The telemetry regulation procedure can also analyze a total amount of telemetry usage by the implantable device 104 within a defined time period (e.g., a twenty four hour period). For example, the telemetry regulation procedure can monitor an amount of time telemetry operations of the implantable device 104 are active or turned on, referred to herein as on-time (e.g., wherein active or turned on telemetry operations include activation of a receiver and/or a transmitter of the implantable device 104). The telemetry regulation procedure can further compare a monitored duration of telemetry on-time within a defined period of time against a threshold on-time duration (e.g., of N minutes) allowed for the defined period of time. In another example, the telemetry regulation procedure can monitor an amount of data transferred between the implantable device 104 and the external device 116 within a defined period of time. The telemetry regulation procedure can further compare a monitored amount of data transferred within the period of time against a threshold data transfer amount (e.g., M megabytes (MB)) for the period of time.

Based on analysis of one or more of the above factors, the implantable device 104 can determine whether to disable or prevent future telemetry with an unauthorized external device (e.g., external device 116) and the duration for which to disable the future telemetry with the unauthorized external device. In some embodiments, the implantable device 104 can also determine whether to disable or prevent future telemetry with the unauthorized external device and other external devices (e.g., other external devices can be any external device that may attempt to communicate with the implantable device 104, in some cases). In some implementations, in response to a determination that the implantable device 104 should disable or prevent future telemetry with the unauthorized external device and other external devices, the implantable device 104 can determine the duration for which to disable or prevent the telemetry with the unauthorized device and the other unauthorized devices.

In other implementations, the duration can be predefined. For example, the duration can be a predetermined number of minutes or hours. In another example, the defined duration can be a remainder of time left in a monitored time period. For instance, in response to a determination that external device 116 is unauthorized to communicate with the implantable device 104, the implantable device 104 can determine that a total number of unauthorized telemetry requests received by the implantable device 104 within a monitored time period (e.g., a calendar day) exceeds a threshold amount (e.g., ten), and/or a total amount of telemetry communications performed by the implantable device 104 within the monitored time period exceeds another threshold amount (e.g., 0.5 megabytes (MB) of data transferred). In some embodiments, the on-time telemetry can be evaluated. In some embodiments, the on-time telemetry threshold can be 15.5 minutes daily. Based on these determinations, the implantable device 104 can disable or prevent future telemetry with all (or, in some embodiments, one or more) external devices for the remainder of the monitored time period (e.g., the remainder of the calendar day).

In an embodiment, based on a determination to disable or prevent future telemetry with the external device 116 and other external devices for a defined duration, the implantable device 104 can disable or deactivate transmission and/or reception of data packets for the defined duration. For example, the implantable device 104 can be configured to disable or deactivate the transmitter of the implantable device 104 so that packets (e.g., BLE advertisement packets) are not transmitted for the defined duration. In another example, the implantable device 104 can be configured to disable or deactivate the implantable device 104 receiver so that new pairing requests are not received from external devices. Additional details of example embodiments of the subject telemetry regulation procedures are discussed below with respect to FIGS. 2-9.

It is to be appreciated that the implantable device 104 can include one or more devices, transducers and/or circuits that can facilitate telemetry communication and disablement of telemetry communication. For example, the implantable device 104 can include a transmitter that transforms electrical power into a signal associated with transmitted data packets. Additionally, the implantable device 104 can include one or more devices, transducers and/or circuits that can facilitate receiving information from one or more devices (e.g., the external device 116, a server, etc.). For example, the implantable device 104 can include a receiver that transforms a signal into electrical power.

In the example shown in medical device telemetry system 100, a person operating the external device 116 is a patient in which the implantable device 104 is implanted. In another example, another person (e.g., such as medical caregiver) interacting with the patient in which the implantable device 104 is implanted can operate the external device 116 outside the body 102 in which the implantable device 104 is located. In various embodiments, the implantable device 104 can include any number of different types of implantable devices configured to communicate with the external device 116 or another external device. The particular, size, shape, placement and/or function of the implantable device 104 may not be critical to the subject disclosure in some embodiments.

In one embodiment, as mentioned, the implantable device 104 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various embodiments, however, the implantable device 104 can be or include any number of other types of implantable devices that are not IMDs.

For exemplary purposes, the implantable device 104 is illustrated in medical device telemetry system 100 as an IMD implanted within the chest of a patient and configured to provide medical treatment or therapy associated with a heart disease or condition (e.g., an implantable cardioverter-defibrillator (ICD) and/or a pacemaker). In addition to the medical treatment, the implantable device 104 can also be configured to provide the data packetizing and communication operations described herein. The implantable device 104 includes a housing 106 within which electrical components and one or more power sources are housed. The electrical components can be powered via the one or more power sources. A power source (not shown) can include, but is not limited to, a battery, a capacitor, a charge pump, a mechanically derived power source (e.g., microelectromechanical systems (MEMs) device), or an induction component. The various embodiments described herein can provide improved management of power associated with the one or more power sources.

The electrical components can vary depending on the particular features and functionality of the implantable device 104. In various embodiments, these electrical component can include, but are not limited to, one or more processors, memories, transmitters, receivers, transceivers, sensors, sensing circuitry, therapy circuitry, antennas and other components. In an embodiment, the electrical components can be formed on or within a substrate that is placed inside the housing 106. The housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some embodiments, the housing 106 can be a biocompatible housing (e.g., a liquid crystal polymer, etc.).

In the embodiment shown, the implantable device 104 is also an IMD and further includes leads 110*a,b* connected to the housing 106. The leads 110*a,b* extend into the heart and respectively include one or more electrodes. For example, as depicted in medical device telemetry system 100, leads 110*a,b* each include a respective tip electrodes 112*a,b* and ring electrodes 114*a,b* located near a distal end of their respective leads 110*a,b*. When implanted, tip electrodes 112*a,b* and/or ring electrodes 114*a,b* are placed relative to or in a selected tissue, muscle, nerve or other location within the body 102 of the patient. As depicted in medical device telemetry system 100, tip electrodes 112*a,b* are extendable helically shaped electrodes to facilitate fixation of the distal end of leads 110*a,b* to the target location within the body 102 of the patient. In this manner, tip electrodes 112*a,b* are formed to define a fixation mechanism. In other embodiments, one or both of tip electrodes 112*a,b* may be formed to define fixation mechanisms of other structures. In other instances, leads 110*a,b* may include a fixation mechanism separate from tip electrodes 112*a,b*. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110*a,b* are connected at a proximal end of the implantable device 104 via connector block 108. Connector block 108 may include one or more receptacles that interconnect with one or more connector terminals located on the proximal end of leads 110*a,b*. Leads 110*a,b* are ultimately electrically connected to one or more of the electrical components within housing 106. One or more conductors (not shown) extend within leads 110*a,b* from connector block 108 along the length of the lead to engage the ring electrodes 114*a,b* and tip electrodes 112*a,b*, respectively. In this manner, each of tip electrodes 112*a,b* and ring electrodes 114*a,b* is electrically coupled to a respective conductor within its associated lead bodies. For example, a first electrical conductor can extend along the length of the body of lead 110*a* from connector block 108 and electrically couple to tip electrode 112*a* and a second electrical conductor can extend along the length of the body of lead 110*a* from connector block 108 and electrically couple to ring electrode 114*a*. The respective conductors may electrically couple to circuitry, such as a therapy module or a sensing module, of the implantable device 104 via connections in connector block 108. In one or more embodiments, the implantable device 104 is configured to deliver therapy to the heart (or other location) via the electrical conductors to one or more of electrodes 112*a* and 112*b* and 114*a* and 114*b*. In the case of pacing therapy, for example, therapy circuitry within the implantable device 104 can generate and deliver pacing pulses via a unipolar electrode configuration, e.g., using electrodes 112*a* and 112*b* and a housing electrode of the implantable device 104. In other instances, the therapy circuitry within the implantable device 104 can deliver pacing pulses via a bipolar electrode configuration, e.g., using electrodes 112*a* and 112*b* and ring electrodes 114*a* and 114*b*. The therapy circuitry may include one or more pulse generators, capacitors, and/or other components capable of generating and/or storing energy to deliver as pacing therapy in accordance with a pacing regime stored within memory.

Implantable device 104 can also receive sensed electrical signals on the electrical conductors from one or more of electrodes 112*a* and 112*b* and 114*a* and 114*b*. The implantable device 104 can sense the electrical signals using either a unipolar or bipolar electrode configuration. Sensing circuitry of the implantable device 104 may process the sensed electrical signals and the implantable device 104 may analyze the processed and/or or sensed electrical signals and provide the pacing as a function of the sensed electrical signal. The sensing circuitry may include one or more sense amplifiers, filters, rectifiers, threshold detectors, comparators, analog-to-digital converters (ADCs), or other analog or digital components.

The configuration, features and functionality of implantable device 104 are merely provided as an example. In other examples, the implantable device 104 can include more or fewer leads extending from the housing 106. For example, the implantable device 104 can be coupled to three leads, e.g., a third lead implanted within a left ventricle of the heart of the patient. In another example, the implantable device 104 can be coupled to a single lead that is implanted within the ventricle of the heart of the patient. In other embodiments, the lead may be an extravascular lead with the electrodes implanted subcutaneously above the ribcage/sternum or substernally underneath or below the sternum. Example extravascular ICDs having subcutaneous electrodes are described in U.S. Patent Publication No. 2014/0214104 (now U.S. Pat. No. 9,072,914) (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads may include more or fewer electrodes. In instances in which the implantable device 104 is used for therapy other than pacing, (e.g., defibrillation or cardioversion), the leads can include elongated electrodes, which may, in some instances take the form of a coil. The therapy circuitry of the implantable device 104 can generate and deliver defibrillation or cardioversion shocks to the heart via any combination of the elongated electrodes and housing electrode. The therapy circuitry may include one or more high voltage (HV) output capacitors and a HV charging circuit, which may include one or more capacitors, resistors, inductors, transformers, switches, or other analog or digital components, and discharging circuitry to deliver cardioversion or defibrillation therapy, including, for example, an H-bridge circuit. In another embodiment, the implantable device 104 can include leads with a plurality of ring electrodes, (e.g., as used in some implantable neurostimulators), without a tip electrode or with one of the ring electrodes functioning as the "tip electrode."

In another embodiment, the implantable device 104 may include no leads, as in the case of an intracardiac pacemaker or a leadless pressure sensor. In the case of an intracardiac pacemaker, the device may include a housing sized to fit wholly within the patient's heart. In one example, the housing may have a volume that is less than 1.5 cc and, more preferably, less than 1.0 cubic centimeter (cc). However, the housing may be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (now U.S. Pat. No. 8,386,051) (Kenneth), and U.S. Patent Publication No. 2014/0214104 (now U.S. Pat. No. 9,072,914) (Greenhut et al.), each of which is incorporated herein in its entirety. In the case of a leadless pressure sensor, the device can include a housing having a fixation member and a pressure sensing component. One example of a leadless pressure sensor is described in U.S. Patent Publication No. 2012/0108922 (now U.S. Pat. No. 8,475,372) (Schell et al.), which is incorporated herein in its entirety.

External device 116 can include any suitable computing device configured to communicate with implantable device 104. In some embodiments, the external device 116 can be a remote electronic device. For example, external device 116 can include, but is not limited to, a handheld computing device, a mobile phone, a smart phone, a tablet personal computer (PC), a laptop computer, a desktop computer, a personal digital assistant (PDA) and/or a wearable device. In some embodiments, the external device 116 can include a display that can present information associated with the implantable device 104. In another embodiment, the external device 116 can include an application and/or a program associated with the implantable device 104.

Figure 2:
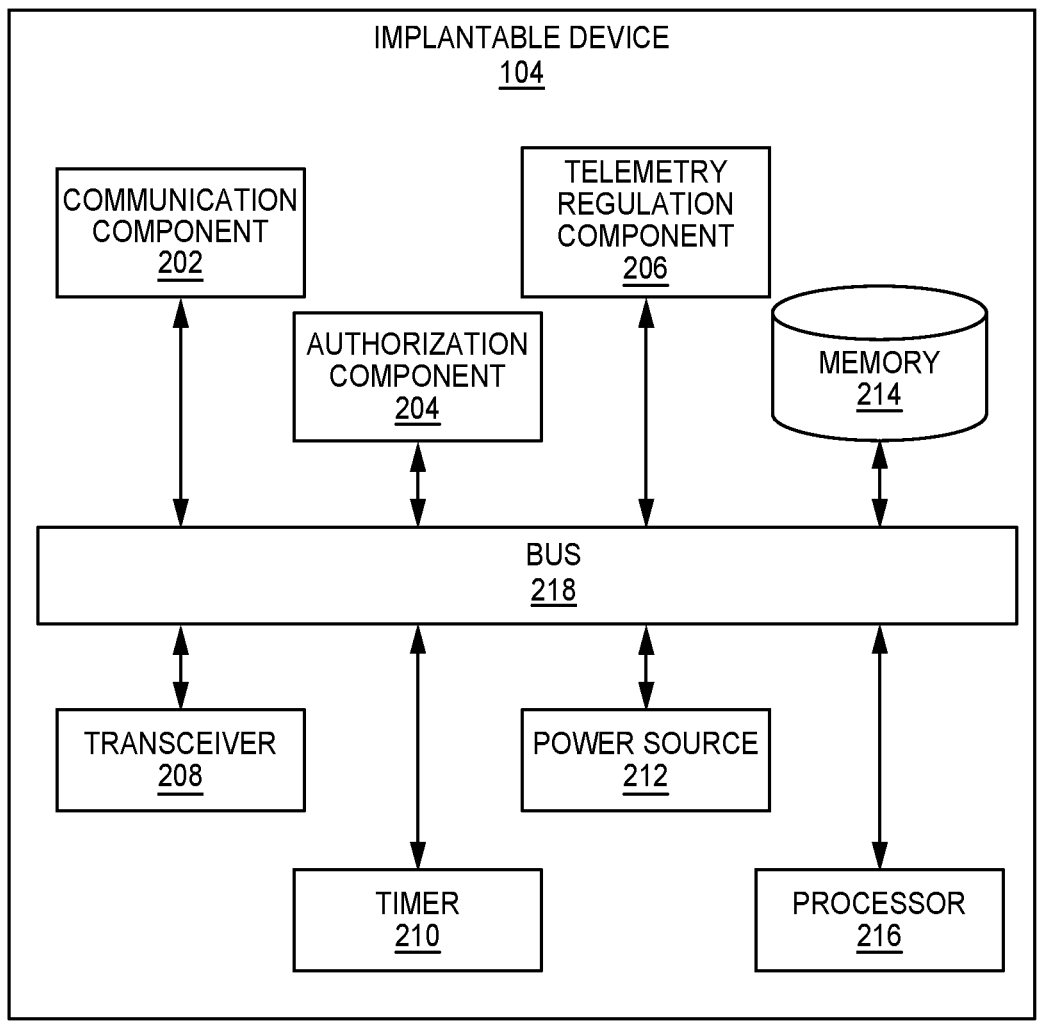
FIG. 2 illustrates a block diagram of an example, non-limiting implantable device in accordance with one or more embodiments described herein.

FIG. 2 illustrates a block diagram of an example, non-limiting implantable device (e.g., implantable device 104) in accordance with one or more embodiments described herein. The implantable device 104 includes communication component 202, authorization component 204, and telemetry regulation component 206. Implantable device 104 also includes a transceiver 208, a timer 210 and a power source 212. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

Implantable device 104 can include memory 214 configured to store computer executable components and instructions. Implantable device 104 can also include a processor 216 to facilitate operation of the instructions (e.g., computer executable components and instructions) by the implantable device 104. Implantable device 104 can include a bus 218 that couples the various components of the implantable device 104, including, but not limited to, the communication component 202, the authorization component 204, the telemetry regulation component 206, the transceiver 208, the timer 210, the power source 212, the processor 216 and/or the memory 214. Repetitive description of like elements employed in other embodiments described herein is omitted for sake of brevity.

With reference to FIGS. 1 and 2, the communication component 202 is configured to facilitate telemetry communication between implantable device 104 and one or more external devices (e.g., external device 116). For example, communication component 202 can control operation of the transceiver 208 (or a transmitter-receiver) to establish a telemetry session with external device 116 and control transmission and reception of data packets by the implantable device 104. In some embodiments, rather than including a transceiver, the implantable device 104 can include a transmitter and a receiver that do not share common circuitry.

Communication component 202 can facilitate telemetry communication between the implantable device 104 and an external device (e.g., external device 116) using a variety of networks (not shown) and/or wireless communication protocols. For example, in one or more embodiments, communication component 202 can communicate with external device 116 using NFC, or another type of communication protocol over a PAN or a LAN, (e.g., a Wi-Fi network) that can provide for communication over greater distances than NFC protocol or that can provide various advantages (such as increased security).

In some embodiments, communication component 202 can control transmission and reception of data packets via a communication channel associated with a communication protocol utilizing lower energy consumption than a conventional communication protocol for wirelessly transmitting data. For example, in a non-limiting example, communication component 202 controls transmission and reception of data packets using BLE protocol. Other communication protocols that can be employed by communication component 202 to communicate with external device 116 can include, but are not limited to, other BLUETOOTH® communication protocols, a Session Initiation Protocol (SIP) based protocol, a Zigbee® protocol, a RF4CE protocol, a WirelessHART protocol, a 6LoWPAN (IPv66 over Low power Wireless Personal Area Network) protocol, a Z-Wave protocol, an ANT protocol, an ultra-wideband (UWB) standard protocol, a radio frequency (RF) communication protocol, and/or other proprietary and non-proprietary communication protocols.

In one or more embodiments, communication component 202 is configured to establish a secure or trusted telemetry session with external device 116 prior to facilitating the exchange of sensitive data between the implantable device 104 and the external device 116. In order to establish such a secure or trusted connection, after the communication component 202 receives a request from an external device (e.g., external device 116) to establish a telemetry session with the implantable device 104 (e.g., after the implantable device 104 and the external device 116 establish an unsecure telemetry connection), the implantable device 104 can determine whether the external device 116 is authorized to communicate with the implantable device 104. Based on a determination that the external device 116 fails to be authorized to communicate with the implantable device 104, in one or more embodiments, the communication component 202 can reject the request from the external device 116, disable the unsecure telemetry connection, and/or forgo establishment of the secure telemetry session with the external device 116.

In some embodiments, authorization component 204 can be configured to determine whether the external device 116 requesting to establish a telemetry session with the implantable device 104 is authorized to communicate with the implantable device 104. The manner in which the authorization component 204 determines whether external device 116 is authorized to communicate with the implantable device 104 can vary based on the telemetry protocol employed by the implantable device 104. For example, in one embodiment, the authorization component 204 is configured to determine whether external device 116 is authorized to communicate with the implantable device 104 based on information provided to the implantable device 104 by the external device 116. In some embodiments, the transmission of this information by the external device 116 to the implantable device 104 is associated with a pairing process employed by the implantable device 104. In other embodiments, the external device 116 can provide this information following reception of an acknowledgment message from the implantable device 104 acknowledging that the implantable device 104 has received the connection request from the external device 116.

For example, in association with sending a request to establish a telemetry session with the implantable device 104, external device 116 can provide the implantable device 104 with information indicating communication parameters for the telemetry session. In some embodiments, the information can also include authentication information for the external device 116 that uniquely identifies the external device 116 (e.g., a device identification number, an encrypted key, a MAC, or other suitable authentication information). The implantable device 104 can process the information to determine whether the external device 116 is authorized to communicate with the implantable device 104.

In various different embodiments, the authorization component 204 can employ one or more different measures as security checks to determine whether the external device 116 is authorized to communicate with the external device 116 based on the received information. For example, the implantable device 104 can determine whether the information has been encrypted with a particular expected key that allows the implantable device 104 to decrypt the information, whether the information includes a valid sequence identifier, whether the information has a valid cyclic redundancy check (CRC), whether the information has a valid MAC and/or whether the information is configured as a valid command Based on a determination that the information fails to pass one or more of these security checks, the authorization component 204 can determine that the external device 116 is unauthorized to communicate with the implantable device 104.

In some embodiments, the authorization component 204 can also determine that an external device 116 is unauthorized to communicate with the implantable device based on a determination that the external device 116 is not communicating in accordance with an aspect of the telemetry protocol employed by the implantable device 104. For example, the authorization component 204 can determine that the external device 116 is unauthorized to communicate with the implantable device 104 based on a determination that the external device 116 fails to provide the implantable device 104 with the required information within a defined window of time (e.g., following establishment of a connection with the external device 116, following initiation of a pairing process with the external device, etc.). For example, the window of time can be a few milliseconds to a few seconds. However, it should be appreciated that this window of time can vary based on the telemetry protocol employed by the implantable device 104.

According to this embodiment, in some implementations, the external device 116 is allowed more than one attempt within the defined time window to prove that the external device 116 is authorized to communicate with the implantable device 104. For example, the external device 116 can communicate two or more downlink data packets to the implantable device within the defined time window. The authorization component 204 can analyze each received downlink packet using the various security checks identified above to determine whether the external device 116 is authorized to communicate with the implantable device 104. If any of the downlink packets received within the defined time window pass authorization, then the authorization component 204 will allow the external device 116 to continue telemetry with the implantable device 104. However, if none of the data packets received within the defined time window pass authorization, the authorization component 204 will declare the external device 116 as unauthorized to communicate with the implantable device 104 and the implantable device 104 will proceed accordingly. In one implementation, the number of attempts allotted for proving authorization can be restricted. For example, the authorization component 204 can tolerate N (e.g., 3) attempts for an external device 116 to prove authorization within the defined time window. After failure to prove authorization at the Nth attempt, the authorization component 204 can declare the external device 116 unauthorized to communicate with the implantable device 104 and proceed accordingly.

In another embodiment, the authorization component 204 can determine that the external device 116 is unauthorized to communicate with the implantable device 104 based on a determination that the external device 116 fails to provide the implantable device 104 with a specific command (e.g., a command including the information) within a defined window of time following reception of the pairing request from the external device 116.

In yet another embodiment, the authorization component 204 can determine that the external device 116 is unauthorized to communicate with the implantable device 104 based on a determination that the external device 116 fails to provide the implantable device 104 with specific information within a defined window of time after a request is sent by the implantable device 104 to the external device 116 for the specific information, or after an acknowledgment message is sent by the implantable device to the external device 116 acknowledging reception of the external device 116 connection request (e.g., a device identifier, an encryption key, etc.).

It should be appreciated that other suitable mechanisms can be employed by the authorization component 204 to determine whether an external device 116 is authorized to communicate with the implantable device 104 based on the authorization process associated with the telemetry protocol employed by the implantable device 104.

In some embodiments described herein, the authorization component 204 can erroneously determine that the external device 116 is unauthorized to communicate with the implantable device 104 in an instance in which the external device is authorized to communicate with the implantable device 104. For example, the authorization component 204 can determine that external device 116 is unauthorized to communicate with the implantable device 104 based on a failure to receive information from the external device 116 within a defined window of time due to a weak telemetry connection between the external device 116 and the implantable device 104. Yet the external device 116 may, in fact, be authorized to communicate with the implantable device 104, and therefore, the external device 116 is not performing an intentional battery drainage communications event. Nevertheless, by characterizing the external device 116 as an unauthorized device for communication purposes, fruitless power consuming attempts made by an authorized external device to communicate with the implantable device 104 can be regulated.

In some embodiments, the telemetry regulation component 206 can monitor or track telemetry session requests received by the implantable device 104 from devices that fail authorization. Telemetry session requests received from external devices that fail authorization are referred to herein as "unauthorized telemetry requests." Information regarding tracked unauthorized telemetry requests can be stored by the implantable device 104 in memory 214. Based on analysis of the unauthorized telemetry requests, the telemetry regulation component 206 can determine whether to disable one or more (or, in some embodiments, all) telemetry capabilities of the implantable device 104.

In some embodiments, the telemetry regulation component 206 can also determine an amount of time to disable the telemetry capabilities of the implantable device 104. Telemetry regulation component 206 can also generate a signal that can cause communication component 202 to disable telemetry performance by the implantable device 104 accordingly (e.g., deactivate a transmitter, a receiver, or a transceiver of the implantable device 104).

In particular, in some embodiments, telemetry regulation component 206 can monitor or track information regarding the number of unauthorized telemetry requests received by the implantable device 104 in a defined period of time. For example, the defined period of time can include a week, a twenty four hour period (e.g., a calendar day), a twelve hour period, or another suitable time period.

Telemetry regulation component 206 can employ a timer 210 (or clock) of the implantable device 104 to keep track of the defined time period. In one implementation, the telemetry regulation component 206 can timestamp the respective unauthorized telemetry requests received by the implantable device 104. According to this implementation, the telemetry regulation component 206 can also monitor the duration between reception of unauthorized telemetry requests and/or frequency of received unauthorized telemetry requests in a defined window of time (e.g., a minute window, a five minute window, an hour window, or another suitable defined window of time).

The telemetry regulation component 206 can also monitor information identifying the unauthorized devices from which the unauthorized telemetry requests were received. As used herein, monitoring can also include, but is not limited to, processing, storing and/or analyzing. The telemetry regulation component 206 can also monitor information identifying the reason or reasons for determining that an external device was deemed unauthorized to communicate with the implantable device 104.

The telemetry regulation component 206 can also monitor an amount of telemetry usage employed by the implantable device 104 within a defined time period (e.g., a twenty four hour period). For example, the telemetry regulation component 206 can monitor implantable device 104 on-time within a defined period of time (e.g., in minutes and seconds). In another example, the telemetry regulation component 206 can monitor an amount of data transferred between the implantable device 104 and the external device 116 within the defined period of time (e.g., M megabytes (MB)).

In various additional embodiments, the telemetry regulation component 206 is configured to monitor or track information identifying attempts made by external devices (e.g., external device 116) to open a telemetry session with the implantable device 104 that are aborted before a defined time window applied by the implantable device 104 for the external device 116 to prove authorization. For example, as discussed above, in some embodiments, the implantable device 104 can allow the external device 116 a defined window of time (e.g., 3 seconds) to prove that the external device 116 is authorized to communicate with the implantable device 104 after initial reception of a request from the external device 116 to communicate with the implantable device 116. In some scenarios, the external device 116 can abort attempting to prove authorization within this defined time window (e.g., at 2 seconds or 2.5 seconds) or otherwise disconnect from the implantable device 104 within this defined time window to avoid being declared unauthorized to communicate with the implantable device 106 by the authorization component 204.

For example, after the external device 116 establishes an initial connection with the implantable device 104 in association with a request to establish an authorized telemetry session with the implantable device 104, the external device 116 can decide to disconnect from the implantable device 104. Upon disconnection, the implantable device 104 can receive an indication or notification that the external device 116 has disconnected from the implantable device 104. In other scenarios, after the external device 116 establishes an initial connection with the implantable device 104, the external device 116 and the implantable device 104 can become disconnected for other reasons prior to expiration of the allotted window of time for proving authorization (e.g., the external device 116 can stop communicating with the implantable device 104 due to various reasons, the implantable device 104 transceiver may experience an issue and reset, etc.).

In these scenarios, the telemetry regulation component 206 can track information identifying when, how and/or why an initial telemetry connection established between the external device 116 and the implantable device 104 becomes disconnected prior to expiration of the allotted window of time for the external device to prove authorization. The telemetry regulation component can further employ this information to facilitate determining whether, when and/or for how long to disable telemetry performance by the implantable device 104.

In accordance with various embodiments, each time (or, in some embodiments, one or more times that) the authorization component 204 determines that an external device (e.g., external device 116) requesting to establish a telemetry session with the implantable device 104 is unauthorized to communicate with the implantable device 104, the telemetry regulation component 206 can perform a telemetry regulation procedure. The telemetry regulation component 206 can also perform a telemetry regulation procedure based on tracked information regarding aborted or disconnected telemetry connections between the external device 116 and the implantable device 104 prior to expiration of a time window allotted for the external device 116 to prove authorization. The telemetry regulation procedure can be a procedure designed to minimize or prevent the occurrence of intentional battery drainage communications from unauthorized external devices and/or regulate an amount of telemetry conducted by the implantable device 104 with authorized devices to prevent battery overuse by the implantable device.

In one or more embodiments, performance of the telemetry regulation procedure by telemetry regulation component 206 involves analysis of information including, but not limited to, an amount (e.g., a number) of unauthorized telemetry requests received from a particular external device 116 within a defined period of time (e.g., a twenty four hour period), a frequency of unauthorized telemetry requests received from a particular external device within a defined window of time (e.g., five minutes, ten minutes, one hour, five hours, etc.), an amount of unauthorized telemetry requests received by the implantable device 104 from one or more external devices within a defined period of time, and/or a frequency of unauthorized telemetry requests received by the implantable device 104 from one or more external devices within a defined window of time. The telemetry regulation procedure can also involve analysis of an amount of telemetry usage employed by the implantable device 104 within a defined time period (e.g., a twenty four hour period). In some implementations, the telemetry regulation procedure also involves analysis of the reason or reasons for determining that respective external devices were unauthorized to communicate with the implantable device 104. In some implementations, performance of the telemetry regulation procedure by telemetry regulation component 206 also involves analysis of information including amount, frequency, and cause of aborted or disconnected telemetry connections between the external device 116 and the implantable device 104 prior to expiration of a time window allotted for the external device 116 to prove authorization.

Based on analysis of one or more of the above noted factors, the telemetry regulation component 206 is configured to determine whether to disable or prevent future telemetry with the unauthorized external device 116 and other external devices for a defined duration (e.g., the implantable device 104 telemetry capabilities can be deactivated so that no telemetry communication can be performed by the implantable device 104). The defined duration can be a defined duration, such as a defined number of minutes or hours. In some implantations, the defined duration can be a remainder of time left in a monitored time period. In other implementations, the telemetry regulation component 206 can determine the defined duration based on one or more of the factors above. In some embodiments, the defined duration can be predetermined prior to initialization of the implantable device 104 and/or updated from time to time (e.g., the implantable device 104 can be programmed, re-programmed, configured or re-configured to adhere to different defined durations during which no telemetry communication can be performed).

In various embodiments, to disable or prevent future telemetry with external device 116 and other external devices for the defined duration, the telemetry regulation component 206 can direct communication component 202 to disable or deactivate transmission and/or reception of data packets for the defined duration. For example, the communication component 202 can disable or deactivate a transceiver 208 or transmitter of the implantable device 104 so that packets (e.g., BLE advertisement packets) are not transmitted for the defined duration. In another example, the communication component 202 can disable or deactivate a transceiver 208 or receiver of the implantable device 104 so that new connection requests are not received by the implantable device 104 from external devices (e.g., external device 116 and other external devices).

In another embodiment, in addition, or in the alternative, to disabling future telemetry with an unauthorized external device 116 and other external devices, the telemetry regulation component 206 can store information (e.g., in memory 214) associating the unauthorized external device 116 as a device that the implantable device 104 should not communicate with in the future. For example, the telemetry regulation component 206 can associate the unauthorized external device 116 with a list that identifies unauthorized devices. After an unauthorized external device is associated with the list, the communication component 202 can ignore future connection requests received from the unauthorized external device. In some implementations, the telemetry regulation component 206 can employ a threshold requirement for an amount of failed authorization attempts prior to associating an external device with the list. For example, the telemetry regulation component 206 can associate an external device with the list of unauthorized devices if the external device fails to pass authorization after N attempts (e.g., five attempts) within a time period (e.g., a 24 hour period) monitored by the implantable device 104. In another example, the telemetry regulation component 206 can associate an external device with the list of unauthorized devices if the external device fails to pass authorization after M attempts within a defined time window (e.g., 3 attempts in five minutes). According to this embodiment, based on a determination that an external device 116 is unauthorized to communicate with the implantable device 104, the telemetry regulation component 206 can prevent future telemetry between the implantable device 104 and the external device 116 while allowing future telemetry with the implantable device 104 and other external devices.

Still in other embodiments, as an alternative to disabling future telemetry with the unauthorized external device 116, or disabling future telemetry with the other external devices, the implantable device 104 can employ a secondary telemetry communication protocol. For example, based on a determination that telemetry communication between the external device 116 and the implantable device 104 or between the external device 104 and other external devices (including external device 116) should be disabled for a defined duration of time, the telemetry regulation component 206 can direct communication component 202 to employ a secondary telemetry communication apparatus or protocol for the defined duration that enables the implantable device 104 to only communicate with other authorized external devices that also employ the secondary communication protocol. In this scenario, known secure or dedicated devices (e.g., an administrator device, a device operated by a physician of the patient) can continue to communicate with the implantable device 104. The secondary telemetry communication apparatus or protocol can vary. For example, the secondary telemetry communication apparatus or protocol can include, but is not limited to, NFC, inductive communication, or a proprietary (e.g., non-commercially available) telemetry communication protocol.

In one embodiment, the telemetry regulation component 206 employs a threshold based analysis with respect to a maximum number of received unauthorized telemetry requests within a defined period of time to determine whether to disable telemetry. For example, in response to a determination that external device 116 fails to pass authorization after N attempts within a defined period of time (e.g., a calendar day), the telemetry regulation component 206 can direct communication component 202 to disable or prevent future telemetry with the external device 116 and/or disable future telemetry with other external devices for another defined period of time (e.g., a remainder of the calendar day). In another example, based on a determination that the implantable device 104 has received M telemetry requests from one or more external devices (e.g., including external device 116) determined to be unauthorized to communicate with the implantable device 104 within a defined period of time (e.g., a calendar day), the telemetry regulation component 206 can direct communication component 202 to disable or prevent future telemetry with the external device 116 and/or other external devices for another defined period of time (e.g., a remainder of the calendar day). Likewise, based on a determination that an amount of unauthorized telemetry requests received does not exceed the threshold amount, the telemetry regulation component 206 can direct the communication component 202 to maintain enablement of telemetry communication according to the telemetry protocol employed by the implantable device 104.

The telemetry regulation component 206 can also employ a threshold based analysis with respect to a maximum number of received aborted or disconnected telemetry requests within a defined period of time to determine whether to disable telemetry. For example, in response to a determination that over a defined time period (e.g., calendar day), the external device 116 connected with the implantable device 104 and disconnected or aborted the connection, more than N times, within a defined time window allotted for proving authorization, the telemetry regulation component 206 can direct communication component 202 to disable or prevent future telemetry with the external device 116 and/or disable future telemetry with other external devices for another defined period of time (e.g., a remainder of the calendar day). In another example, based on a determination that the implantable device 104 has received M aborted or disconnected telemetry requests from one or more external devices within a defined period of time (e.g., a calendar day), the telemetry regulation component 206 can direct communication component 202 to disable or prevent future telemetry with the external device 116 and/or other external devices for another defined period of time (e.g., a remainder of the calendar day).

In another embodiment, the telemetry regulation component 206 can determine whether to disable telemetry based on a frequency threshold with respect to reception of unauthorized telemetry requests and/or prematurely aborted/disconnected telemetry requests. For example, in response to a determination that the implantable device 104 has received N unauthorized and/or aborted/disconnected telemetry requests from an external device 116 within a M minute window of time (e.g., five minutes), the telemetry regulation component 206 can direct communication component 202 to disable or prevent future telemetry with the external device 116 and other external devices for a defined duration (e.g., the following hour). In another example, in response to a determination that the implantable device 104 has received N unauthorized and/or aborted/disconnected telemetry requests from one or more external devices (e.g., including external device 116) within a M minute window of time, the telemetry regulation component 206 can direct communication component 202 to disable or prevent future telemetry with the external device 116 and other external devices for a defined duration (e.g., the following hour) Likewise, in response to a determination that a frequency of unauthorized telemetry requests received fails to exceed the threshold amount, the telemetry regulation component 206 can direct the communication component 202 to maintain enablement of telemetry communication according to the telemetry protocol employed by the implantable device 104.

The telemetry regulation component 206 can also determine whether to disable telemetry based on a threshold amount of telemetry performance allowed for the implantable device 104 within a defined period of time (e.g., determined as a function of data consumption or duration of telemetry communications). For example, after a determination that external device 116 is unauthorized to communicate with the implantable device 104, the telemetry regulation component 206 can analyze an amount of telemetry usage or consumption by the implantable device 104 within a defined time period (e.g., the current calendar day or another suitable time period). If the amount of telemetry usage exceeds a threshold amount, the telemetry regulation component 206 can direct the communication component 202 to disable or prevent telemetry with the external device 116 and/or other external devices for another period of time (e.g., a remainder of the calendar day). Likewise, in response to a determination that an amount of telemetry usage during the time period fails to exceed the threshold amount, the telemetry regulation component 206 can direct the communication component 202 to maintain enablement of telemetry communication according to the telemetry protocol employed by the implantable device 104. In another example, after a determination that external device 116 prematurely aborted or disconnected from the implantable device 104 within the allotted time period for proving authorization, the telemetry regulation component 206 can analyze an amount of telemetry usage or consumption by the implantable device 104 within a defined time period (e.g., the current calendar day or another suitable time period). If the amount of telemetry usage exceeds another threshold amount, the telemetry regulation component 206 can direct the communication component 202 to disable or prevent telemetry with the external device 116 and/or other external devices for another period of time (e.g., a remainder of the calendar day).

In some embodiments, the telemetry regulation component 206 can determine whether to disable telemetry based on a combination of the above factors. For example, after reception of an unauthorized or aborted/disconnected telemetry request, the telemetry regulation component 206 can analyze an amount or frequency of received unauthorized telemetry requests within a defined period of time, an amount or frequency of received aborted/disconnected telemetry requests within the defined time period, and an amount of telemetry usage of the implantable device 104 within the defined period of time. For example, after an unauthorized telemetry request is received from an external device 116, the telemetry regulation component 206 can determine that future telemetry with the unauthorized external device 116 and/or other external devices should be disabled for a defined duration of time based on an amount of unauthorized and/or aborted/disconnected telemetry requests received in a defined period of time exceeding a threshold amount, and an amount of telemetry usage by the implantable device within the defined period of time exceeding the threshold amount.

In various additional embodiments, the telemetry regulation component 206 can determine whether to disable telemetry based on a distribution or pattern with respect to the types of unauthorized telemetry requests received by the implantable device 104. According to these embodiments, a type of unauthorized telemetry request can refer to the reason or reasons for which the authorization component 204 determined an external device 116 to be unauthorized to communicate with the implantable device 104. In particular, as discussed herein, the authorization component 204 can determine that an external device 116 is unauthorized to communicate with the implantable device 104 based on a variety of factors, such as, but not limited to, failure to receive information at the implantable device 104 from the external device 116 within a defined window of time, failure of the information to pass decryption, failure of the information to include a valid sequence identifier, failure of a packet of the information to have a valid CRC, failure of the information to have a valid MAC, failure of the information to be a valid command and/or failure of the information to conform to the telemetry protocol employed by the implantable device 104. Thus, in some embodiments, the telemetry regulation component 206 can track when an unauthorized telemetry request is received, the identity of the device from which the unauthorized telemetry request was received, and the reason or reasons for determining that the device was unauthorized for telemetry with the implantable device 104.

For example, in one embodiment, the telemetry regulation component 206 can associate different severity weights with the different types of unauthorized telemetry requests that reflect a degree of severity or security concern associated with the respective types of unauthorized telemetry requests (e.g., a failure to receive a packet can be associated with higher weight than a failure to pass decryption). The telemetry regulation component 206 can employ these weights to calculate a telemetry regulation score for the implantable device 104 for each of (or, in some embodiments, one or more of) the monitored periods of time. The telemetry regulation can reflect a number of unauthorized telemetry requests received in the period of time and the types of unauthorized telemetry requests received in the period of time. For example, the greater the number of more severely weighted unauthorized telemetry requests, the higher the telemetry regulation score. In some implementations, the telemetry regulation score can also reflect an amount of telemetry usage by the implantable device 104 within the defined period of time. For example, the amount of telemetry usage within the defined period of time can serve as a multiplier in the telemetry regulation score calculation, such that the greater the amount of telemetry usage, the higher the score.

According to this embodiment, the telemetry regulation component 206 can calculate or re-calculate a telemetry regulation score for the implantable device 104 based on receipt of a new unauthorized authentication telemetry request from an external device 116 within the defined period of time. The telemetry regulation component 206 can further direct communication component 202 to disable or prevent future telemetry with the external device 116 and/or other external devices based on the telemetry regulation score exceeding a threshold value.

In another embodiment, the telemetry regulation component 206 can determine whether to disable or prevent future telemetry with an unauthorized device and/or other external devices based on a pattern in the types of failed authorization telemetry requests received. Respective patterns can be associated with information accessible to the telemetry regulation component 206 (e.g., in memory 214) that correlates certain patterns with a determination to disable or prevent telemetry. Based on observation of a pattern in received unauthorized telemetry requests that is associated with a determination to disable or prevent telemetry, the telemetry regulation component 206 can be configured to direct communication component 202 to disable telemetry accordingly. For example, the telemetry regulation component 206 can determine to disable telemetry in response to reception of three sequential same types of unauthorized telemetry requests in a row (e.g., connection requests that failed authorization based on failure to provide a packet in association with the pairing procedure employed by the implantable device 104). In another example, the telemetry regulation component 206 can determine that telemetry capabilities of the implantable device 104 should not be disabled based on reception of a first type of unauthorized telemetry request, followed by a second type of unauthorized telemetry request, further followed by a third type of telemetry request. According to this embodiment, in addition to type of unauthorized telemetry request, the telemetry regulation component 206 can also analyze patterns associated with the devices from which unauthorized telemetry requests are received and the duration between received unauthorized telemetry requests.

As discussed above, in various embodiments the duration of telemetry disablement can be predetermined and/or changed from time to time. For example, regardless of the reason for determining that telemetry with an unauthorized external device 116 and/or other external devices should be disabled, the duration of disablement can be a defined period of time, such as one hour, three hours, a remainder of the monitored time period, etc. In some embodiments however, the duration of time for telemetry disablement can be determined by the telemetry regulation component 206 based on the reason for determining that telemetry should be disabled. For example, in response to a determination that telemetry should be disabled because the implantable device 104 has exceeded a threshold telemetry usage amount for a monitored time period, the duration of time for telemetry disablement can be set to the remainder of the monitored time period (e.g., regardless of the duration of the remainder of the monitored time period). In another example, in a response to a determination that a number of unauthorized telemetry requests received in a monitored period of time exceed a threshold amount, the duration of telemetry disablement can be set to N hours or a remainder of the monitored time period, whichever is greater. In another example, in response to a determination that telemetry should be disabled based on a frequency of received unauthorized telemetry requests within a defined window exceeding a threshold (e.g., a spike in unauthorized telemetry requests), the telemetry regulation component 206 can disable telemetry for M minuets (e.g., 30 minutes, 60 minutes, etc.).

In another embodiment, the telemetry regulation component 206 can determine duration of time for which to disable telemetry based on a calculated telemetry regulation score. According to this embodiment, the telemetry regulation component 206 can be configured to determine to disable telemetry based on a reception of a threshold number of unauthorized telemetry requests and/or a total amount of telemetry usage by the implantable device 104 within a defined time period (e.g., a twenty four hour period). However, in lieu of disabling telemetry for a set amount of time (e.g., one hour, two hours, the remainder of the defined time period, etc.), the telemetry regulation component 206 can determine a tailored period of time to disable telemetry based on a calculated telemetry regulation score for the monitored period of time. As discussed above, the telemetry regulation score can reflect a number and type of received unauthorized telemetry requests and an amount of telemetry consumption by the implantable device during the monitored time period. For example, different telemetry regulation scores can be associated with different durations of telemetry disablement and higher scores can be associated with longer durations than lower scores.

In yet another example, the telemetry regulation component 206 can determine duration for telemetry disablement based on a pattern associated with received unauthorized telemetry requests, wherein respective patterns are associated with different durations.

The telemetry regulation component 206 can also determine the duration of time to disable telemetry based on a context of the implantable device 104, including, but not limited to, a time of day and/or a location of the implantable device 104. For example, in association with performing telemetry regulation to minimize or prevent battery depletion due to malicious events (e.g., intentional battery drainage communications), a certain time of day can be considered more critical or high risk than another time of day. In particular, depending on the time of day, a wearer of the implantable device 104 will be located within proximity to more or less external devices that are suspected or deemed to have previously performed malicious events. For example, in the early morning or late evening hours, an individual may be less likely to be near other people (and their associated electronic devices) that the user does not trust relative to other times of the day. Accordingly, the possibility of scenarios of malicious events is decreased. Therefore, in response to a determination that telemetry should be disabled within or near a time considered low risk for malicious events, the telemetry regulation component

206 can disable telemetry for a shorter time period than a time period considered to be higher risk for malicious events.

Similarly, certain locations can be considered higher risk for malicious events relative to other locations. For example, a home or the wearer of the implantable device 104, a hospital, a doctor's office, etc., could be considered low risk locations, while more public locations (e.g., a shopping center, a movie theater, a workplace, etc.) could be considered higher risk locations. Thus in some implementations, the implantable device 104 can be configured to determine its location using various known locating techniques (e.g., global positioning system based techniques, triangulation, detection of a known signal associated with a particular location, etc.). The telemetry regulation component 206 can further determine, based on defined information, a risk level associated with a current location of the implantable device 104. For example, if the implantable device is not located within a location that has been determined to be a low risk location, the implantable device can be considered to be in a high risk location by default. Based on a determination that telemetry should be disabled, the telemetry regulation component 206 can further determine the duration for disablement based on the location of the implantable device 104. For example, a high risk location can be associated with a lower duration than a low risk location.

In some additional embodiments, the telemetry regulation component 206 can also determine whether and for how long the implantable device 104 should stop or disable telemetry communication based on a remaining power level of the implantable device 104. For example, over time as the battery level of the implantable device 104 decreases, the telemetry regulation component 206 can increase a preset duration of time that the implantable device disables telemetry following a determination that telemetry should be disabled. In another example, as the battery level of the implantable device 104 decreases, in association with telemetry regulation analysis, the telemetry regulation component 206 can reduce the threshold amount of unauthorized telemetry requests associated with disabling telemetry and/or reduce a threshold amount of total telemetry usage allotted for a defined period associated with disabling telemetry.

Implantable device 104 further includes a suitable power source 212 to drive the functionality of implantable device 104 and provide power to the various electrical components of the implantable device 104. In one or more embodiments, the power source includes but is not limited to, a battery, a capacitor, a charge pump, a mechanically derived power source (e.g., microelectromechanical systems (MEMs) device), or an induction component. The various embodiments described herein can provide improved management of power associated with the power source 212. The telemetry regulation embodiments described herein can prevent or minimize unnecessary and excessive usage of the power source 212 of the implantable device 104, thereby increasing the lifespan of the implantable device 104.

FIG. 3A illustrates an example, non-limiting table including telemetry regulation information monitored over a period of time by an implantable device (e.g., implantable device 104) and not resulting in disabled telemetry performance in accordance with one or more embodiments described herein. FIG. 3B illustrates an example, non-limiting table including telemetry regulation information monitored over a period of time by an implantable device (e.g., implantable device 104) and resulting in disabled telemetry performance to minimize telemetry overuse in accordance with one or more embodiments described herein.

With reference to FIGS. 1, 2, 3A and 3B, in accordance with the example tables of FIGS. 3A and 3B, the telemetry regulation component 206 is configured to determine whether to disable telemetry (e.g., prevent future transmission and/or reception of data by the implantable device 104) for a remainder of the 24 hour period based on reception of three unauthorized telemetry requests from a same external device within the 24 hour period. FIG. 3A depicts a scenario in which telemetry was not disabled during the 24 hour period because although two instances of reception of two unauthorized telemetry requests from two different devices (e.g., device ID 775632 and 459987) occurred, three unauthorized telemetry requests were not received from a same device during the 24 hour period.

FIG. 3B depicts an example scenario wherein three unauthorized telemetry requests were received by the implantable device 104 from a same device (e.g., device ID 775632) within the 24 hour period. Upon reception of the third unauthorized telemetry request from device ID 775632, telemetry is then disabled for a remainder of the 24 hour period (e.g., from time 17:09 to time 24:00). However, as discussed supra, other possible durations of telemetry disablement can be used. In some embodiments as discussed supra, in addition to or in the alternative to disabling telemetry for the remainder of the monitored time period, the telemetry regulation component 206 can associate the offending device with a list. The implantable device 104 is further configured to ignore future telemetry communication requests from any devices included in the list.

For example, FIG. 3C illustrates example, non-limiting stored information identifying devices associated with a list of unauthorized devices with which the implantable device (e.g., implantable device 104) will not communicate in accordance with one or more embodiments. According to the example scenario depicted in FIG. 3B, the telemetry regulation component 206 associates device ID number 775632 with the list based on reception of three unauthorized telemetry requests there from. In one implementation, the telemetry regulation component 206 is configured to disable telemetry from 17:09 to 24:00. After beginning of a new 24 hour period (e.g., at 01:01), telemetry by the implantable device 104 is enabled. However based on association of device ID number 775632 with the list, the implantable device 104 will ignore any new telemetry requests from that device. In another implementation, upon reception of three unauthorized telemetry requests from device ID number 775632 at 17:08, the telemetry regulation component 206 can associate device ID number 775632 with the list and ignore any future requests from that device (e.g., for the indefinite future or for a defined time period). However, the implantable device 104 can maintain telemetry communication with other external devices according to standard protocol.

FIG. 4 illustrates an example, non-limiting table including telemetry regulation information monitored over a period of time by an implantable device and resulting in disabled telemetry performance to minimize telemetry overuse in accordance with one or more embodiments described herein. With reference to FIGS. 1, 2 and 4, in accordance with the example table of FIG. 4, the telemetry regulation component 206 is configured to determine whether to disable telemetry (e.g., prevent future transmission and/or reception of data by the implantable device 104) for a remainder of the 24 hour period based on a calculated telemetry regulation score exceeding a threshold value. In accordance with the subject example, the threshold value is a score of 50%. In instances in which a new unauthorized telemetry request is received by the implantable device 104, the telemetry regulation component 206 can determine a telemetry regulation score for the implantable device that reflects a current total amount of unauthorized telemetry requests received, a type of authentication failure of the respective unauthorized telemetry requests, a time at which the request was received, and a total current amount telemetry data usage by the implantable device 104. The type of authentication failure is represented in the table of FIG. 4 with a number code of 1-5. For example, type 1 can refer to a failure to receive a packet from the external device within a defined time window, type 2 can refer to an invalid command, type 3 can refer to a failure to decrypt the downlink packet, type 4 can refer to an invalid sequence ID, and type 5 can refer to an invalid CRC. In some embodiments, the telemetry regulation score can also account for repeat offenders. For example, each additional unauthorized telemetry request received from a same device can be weighted higher.

As shown in FIG. 4, upon reception of the tenth unauthorized telemetry request, the telemetry regulation score increases from 49% to 56%. Accordingly, because the telemetry regulation score exceeds the threshold score value of 50%, telemetry is disabled from time 22:55 to 24:00, a remainder of the monitored 24 hour period. In other embodiments, the duration of the telemetry disablement can be a set duration (e.g., one hour, two hours, etc.) or be determined based on the telemetry regulation score.

FIGS. 5-11 illustrate flow diagrams of example, non-limiting methods that facilitate telemetry overuse reduction in an implantable device (e.g., implantable device 104) in accordance with one or more embodiments described herein. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Figure 5:
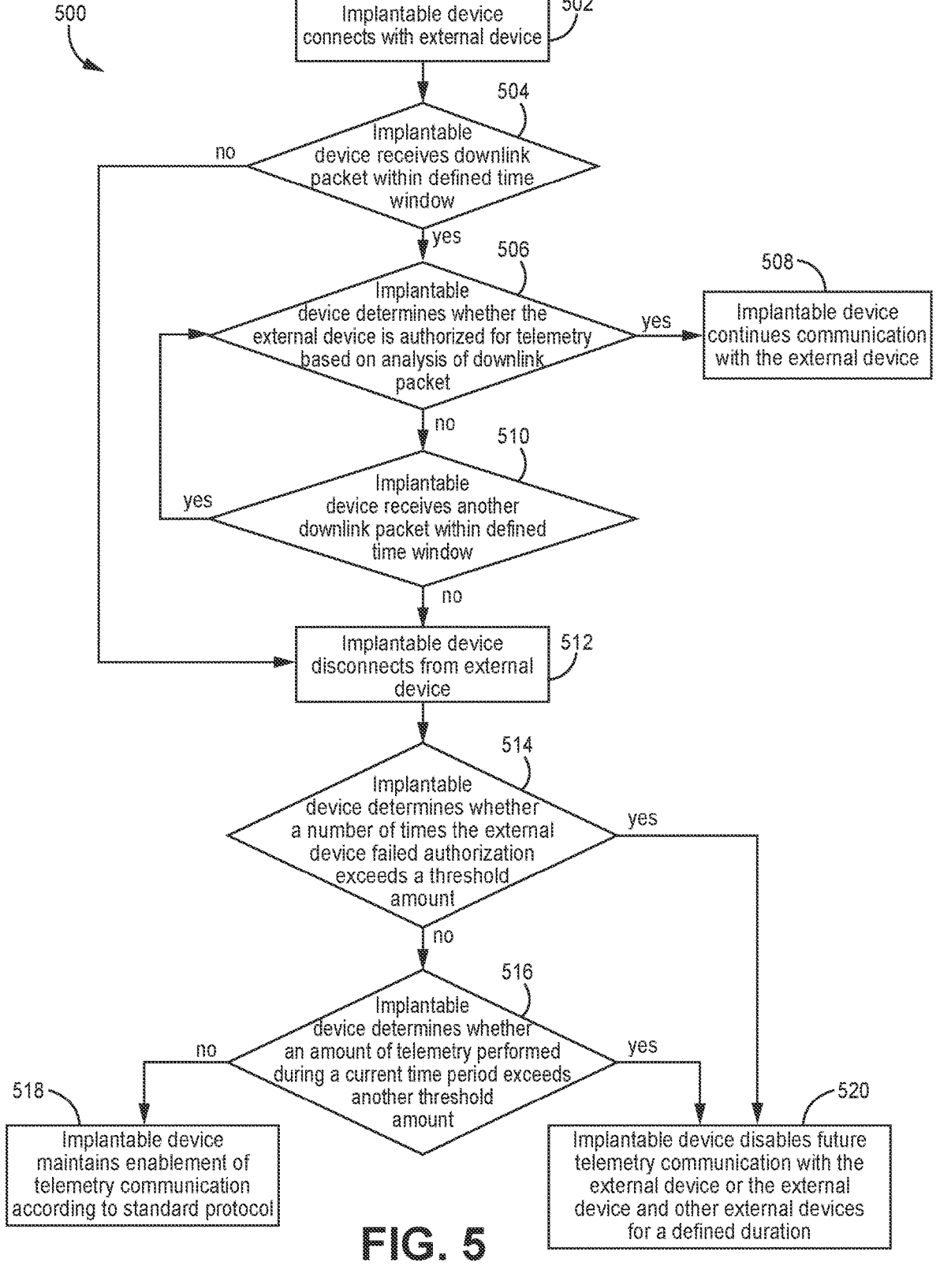

Referring now to FIG. 5, shown is a flow diagram of an example method 500 configured to facilitate telemetry overuse reduction in an implantable device in accordance with one embodiment. In some embodiments of method 500, an implantable device (e.g., implantable device 104) employs a communication component (e.g., communication component 202), an authorization component (e.g., authorization component 204) and a telemetry regulation component (e.g., telemetry regulation component 206) to facilitate minimizing telemetry overuse of the implantable device. Repetitive description of like elements employed in other embodiments described herein is omitted for sake of brevity.

At 502, the implantable device connects with an external device (e.g., external device 116). In one implementation, the implantable device connects with the external device using BLE communication protocol. For example, the implantable device can receive a telemetry connection request from the external device following detection, by the external device, of an advertisement packet sent by the implantable device. In some embodiments, based on reception of the connection request, the implantable device can provide an acknowledgment message back to the external device and/or initiate an authorization procedure during which the implantable device determines whether the external device is authorized to communicate with the implantable device.

In various embodiments, the authorization procedure is associated with a pairing procedure via which the implantable device and the external device exchange information to establish a secure and trusted telemetry connection. In accordance with the authorization procedure employed by the implantable device, the external device provides the implantable device with valid downlink information within a defined window of time after establishing the initial connection with the implantable device. For example, the defined window of time can be a number of milliseconds or seconds following reception of the connection request by the implantable device, following transmission of the acknowledgment message, following a request for the downlink packet sent by the implantable device to the external device, or another suitable trigger. As used herein, downlink information and downlink packets are information and packets, respectively, transmitted from the external device to the implantable device.

At 504, the implantable device determines whether a downlink packet is received within the defined time window. If a downlink packet is not received, the implantable device considers the external device unauthorized and method 500 proceeds to block 512 and the implantable device disconnects from the external device (i.e., the implantable device stops communicating with the external device). If a downlink packet is received within the defined time window, at 506, the implantable device determines whether the external device is authorized to communicate with the implantable device based on analysis of the downlink packet. For example, the implantable device can determine the external device is unauthorized to communicate with the implantable device based on an inability to decrypt the downlink packet, the downlink packet having an invalid sequence identifier, the downlink packet having an invalid CRC, the downlink packet having an invalid MAC, the downlink packet including an invalid command according to the telemetry protocol employed, and other potential security checks. In response to a determination at 506 that the external device is authorized to communicate with the implantable device based on analysis of the downlink packet, at 508, the implantable device continues communication with the external device. For example, the implantable device can establish a secure telemetry session with the external device to exchange sensitive information with the external device. For instance, the sensitive information can include, but is not limited to, physiological data associated with a patient wearing the implantable device and that was sensed by the implantable device. In another example, the sensitive information can include therapy information associated with a therapy delivered by the implantable device to the patient wearing the implantable device.

However, based on a determination at 506 that the external device is unauthorized to communicate with the implantable device, at 510, the implantable device then determines whether another downlink packet is received from the external device within the defined window of time. In response to a decision at 510 that another downlink packet is not received from the external device, the implantable device disconnects from the external device at 512. In response to a decision at 510 that another downlink packet is received from the external device within the defined window of time, the implantable device further proceeds through decisions 506 and 510 again until the defined window of time has passed. In particular, the implantable device analyzes the other downlink packet to determine whether the external device is authorized to communicate with the implantable device. In response to a decision at 506 that the external device is authorized to communicate with the implantable device based on analysis of the other downlink packet, the implantable device continues communication with the external device at 508. In response to a determination that the external device is unauthorized to communicate with the implantable device, the implantable device then determines again whether yet another downlink packet is received from the external device within the defined window of time at 510. In response to a decision that yet another downlink packet is not received within the defined window of time, the implantable device disconnects from the external device at 512.

In addition to disconnecting from the external device, following a determination that the external device is unauthorized to communicate with the implantable device, at 514, the implantable device determines whether a number of times the external device failed authorization exceeds a threshold amount. For example, the implantable device can track telemetry requests received from devices that fail authorization. In some implementations, the implantable device tracks unauthorized telemetry requests received from external devices within a defined window of time (e.g., a calendar day). The implantable device can then determine whether the external device has failed authorization more than a threshold amount. For example, when the threshold amount is two, upon reception of a third failed authorization telemetry request from the external device, the external device will have exceeded the threshold number of allowed unauthorized telemetry request attempts. In response to a determination at 514 that the external device failed authorization more than the threshold amount, method 500 continues to block 520 and the implantable device disables future telemetry with the external device or the external devices and other external devices for a defined duration. For example, in one implementation, the implantable device is configured to prevent the additional communication with the external device for the defined duration but allow additional communication with other external devices. In another implementation, the implantable device is configured to prevent additional communication with the external device and other external devices for the defined duration. For example, the implantable device can deactivate its transceiver so that no data packets are transmitted or received by the implantable device over the defined duration. In response to a determination at 514 that the number of times the external device failed authorization does not exceed the threshold amount, method 500 continues to decision block 516.

At 516, the implantable device determines whether an amount of telemetry performed by the implantable device during a current time period (e.g., a current calendar day), exceeds another threshold amount. For example, the implantable device can determine whether an amount of data usage by the implantable device exceeds a threshold amount allotted for the current time period. In response to a determination that the amount of data usage exceeds the threshold amount, method 500 continues to block 520 wherein the implantable device disables future telemetry with the external device or the external device and other external devices for a defined duration. For example, in one implementation, the implantable device is configured to prevent the additional communication with the external device for the defined duration but allow additional communication with other external devices. In another implementation, the implantable device is configured to prevent additional communication with the external device and other external devices for the defined duration. For example, the implantable device can deactivate its transceiver so that no data packets are transmitted or received by the implantable device over the defined duration. However, in response to a determination at 516 that the amount of data usage by the implantable device does not exceed the threshold amount, method 500 continues to block 518, wherein the implantable device maintains enablement of telemetry communication according to standard protocol (e.g., BLE protocol).

In an alternative embodiment, at 520, the implantable device can deactivate its receiver but maintain activation of its transmitter. According to this embodiment, the implantable device can continue to transmit non-sensitive or non-critical information and/or to transmit information to trusted devices (e.g., using one-way communications), yet refrain from receiving new connection requests from other devices over the defined duration. Still in another alternative embodiment, the implantable device can switch to employing a secondary telemetry communication apparatus or protocol (e.g., NFC, inductive communication, or a proprietary telemetry communication protocol) for the defined duration that facilities telemetry communication between the implantable device and one or more authorized external devices.

Figure 6:
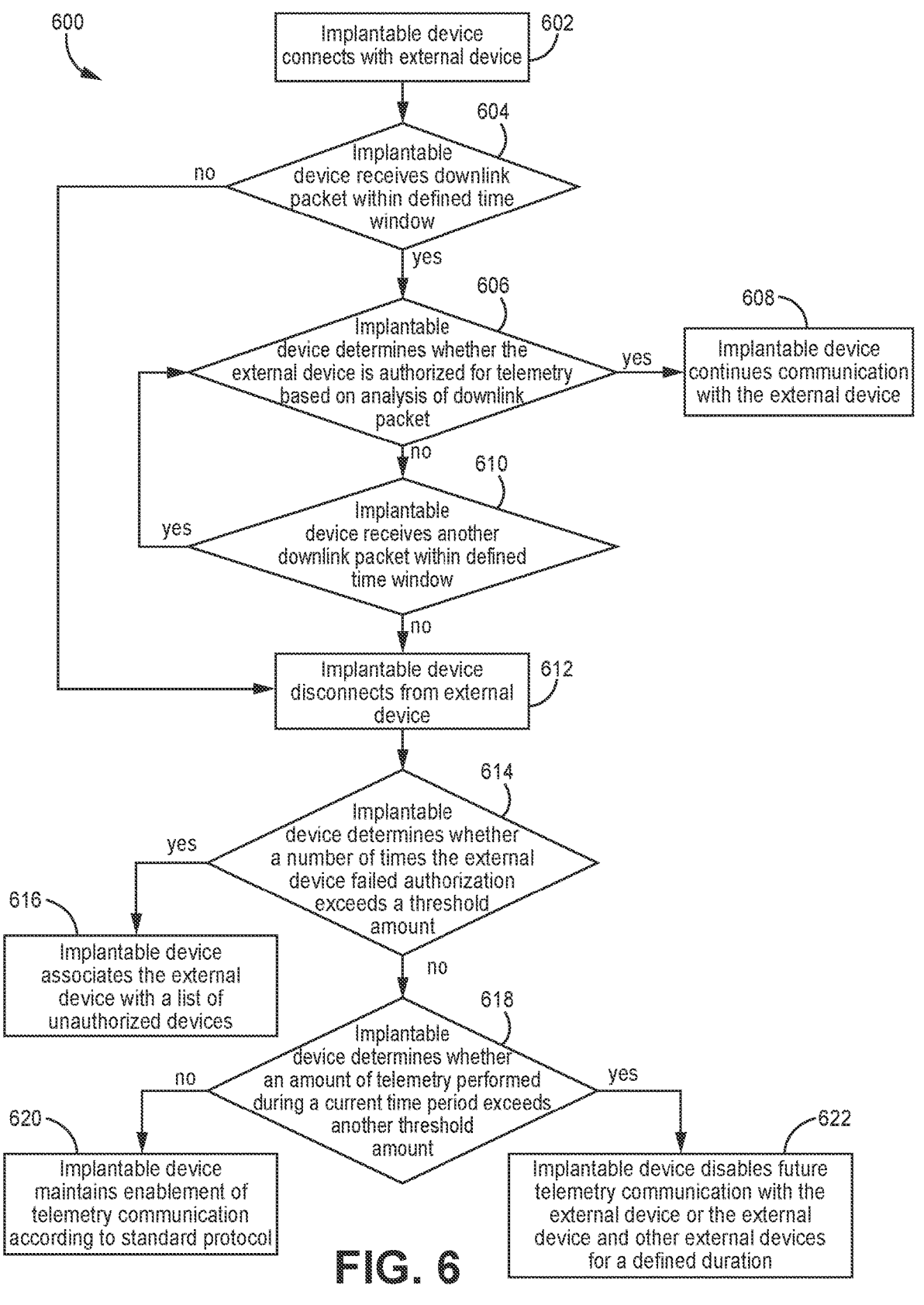

Turning now to FIG. 6, shown is a flow diagram of another example method 600 configured to facilitate telemetry overuse reduction in an implantable device in accordance with another embodiment. In some embodiments of method 600, an implantable device (e.g., implantable device 104) employs a communication component (e.g., communication component 202), an authorization component (e.g., authorization component 204) and a telemetry regulation component (e.g., telemetry regulation component 206) to facilitate minimizing telemetry overuse of the implantable device. Repetitive description of like elements employed in other embodiments described herein is omitted for sake of brevity.

Method 600 can begin in a same or similar manner as method 500. For example, at 602, the implantable device connects with an external device (e.g., external device 116). At 604, the implantable device determines whether a downlink packet is received within the defined time window. If a downlink packet is not received, the implantable device considers the external device unauthorized and method 600 proceeds to block 612 and the implantable device disconnects from the external device (i.e., the implantable device stops communicating with the external device).

If a downlink packet is received within the defined time window, at 606, the implantable device analyzes/processes the downlink packet and determines whether the external device is authorized to communicate with the implantable device. In response to a determination at 606 that the external device is authorized to communicate with the implantable device based on analysis of the downlink packet, at 608, the implantable device continues communication with the external device.

However, based on a determination at 606 that the external device is unauthorized to communicate with the implantable device, the implantable device then determines at 610 whether another downlink packet is received from the external device within the defined window of time. In response to a decision at 610 that another downlink packet is not received from the external device, the implantable device disconnects from the external device at 612. In response to a decision at 610 that another downlink packet is received from the external device within the defined window of time, the implantable device further proceeds through decisions 606 and 610 again until the defined window of time has passed.

In addition to disconnecting from the external device, following a determination that the external device is unauthorized to communicate with the implantable device, at 614, the implantable device determines whether a number of times the external device failed authorization exceeds a threshold amount. In response to a determination at 614 that the external device failed authorization more than the threshold amount, method 600 continues to block 616 and the implantable device associates the external device with a list. For example, the list can include a storage cell of the memory of the implantable device that identifies external devices that the implantable device should not communicate with. Based on associating an external device with the list, the implantable device is configured to reject future telemetry connection requests received from that external device. Accordingly, future telemetry communication between the implantable device and the external device can be prevented indefinitely. However, the implantable device can continue to communicate with other external devices according to standard protocol.

In response to a determination at 614 that the number of times the external device failed authorization does not exceed the threshold amount, method 600 continues to 618. At 618, the implantable device determines whether an amount of telemetry performed by the implantable device during a current time period (e.g., a current calendar day), exceeds another threshold amount. In response to a determination that the amount of data usage exceeds the threshold amount, method 600 continues to block 622 wherein the implantable device disables future telemetry with the external device or the external device and other external devices for a defined duration. For example, in one implementation, the implantable device is configured to prevent the additional communication with the external device for the defined duration but allow additional communication with other external devices. In another implementation, the implantable device is configured to prevent additional communication with the external device and other external devices for the defined duration. For example, the implantable device can deactivate its transceiver so that no data packets are transmitted or received by the implantable device over the defined duration. However, in response to a determination at 618 that the amount of data usage by the implantable device does not exceed the threshold amount, method 600 continues to block 620, wherein the implantable device maintains enablement of telemetry communication according to standard protocol (e.g., BLE protocol).

In an alternative embodiment, at 622, the implantable device can deactivate its receiver but maintain activation of its transmitter. According to this embodiment, the implantable device can continue to transmit non-sensitive or non-critical information and/or to transmit information to trusted devices (e.g., using one-way communications), yet refrain from receiving new connection requests from other devices over the defined duration. Still in another alternative embodiment, the implantable device can switch to employing a secondary telemetry communication apparatus or protocol (e.g., NFC, inductive communication, or a proprietary telemetry communication protocol) for the defined duration that facilities telemetry communication between the implantable device and one or more authorized external devices.

Figure 7:
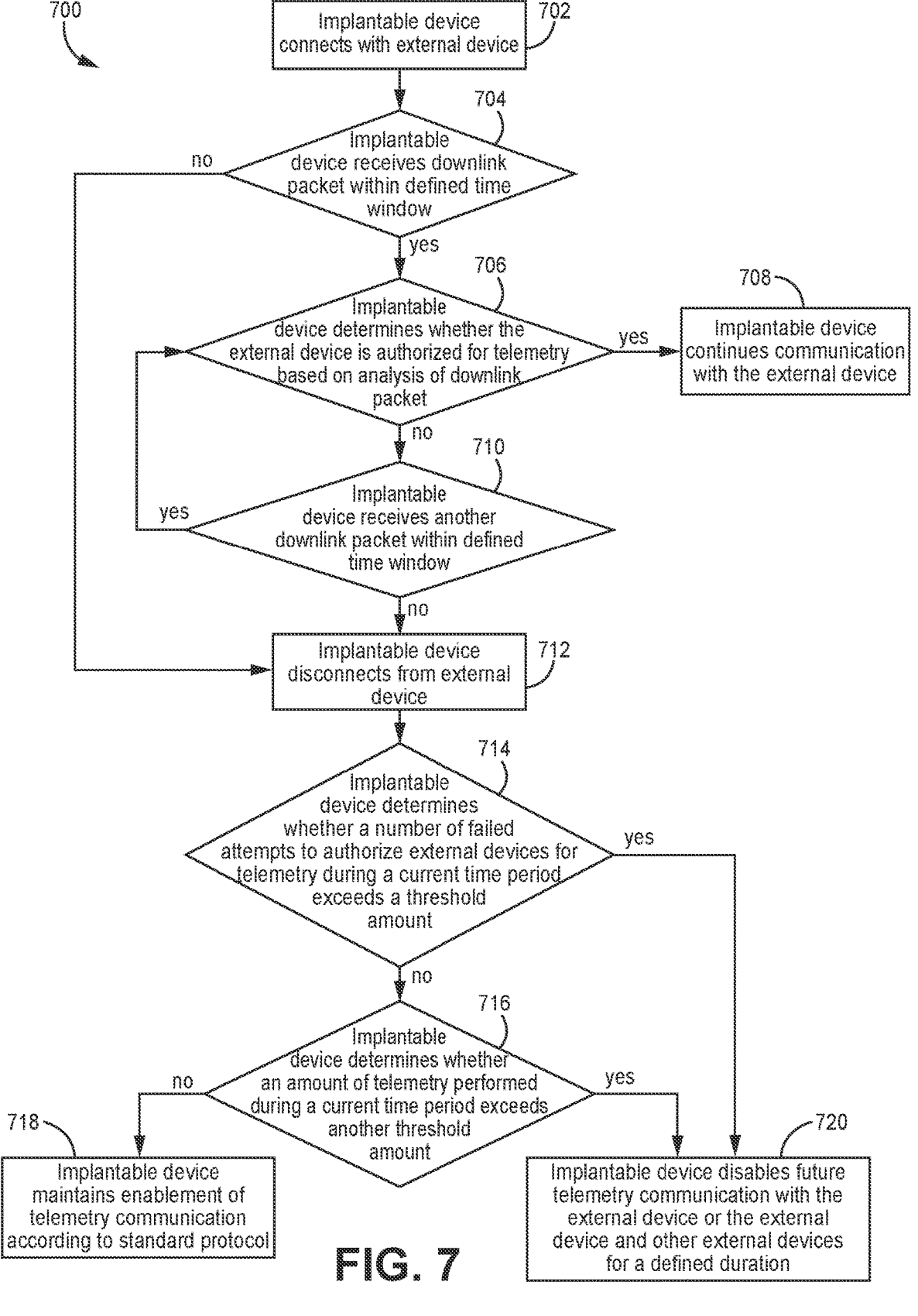

FIG. 7 presents a flow diagram of another example method 700 configured to facilitate telemetry overuse reduction in an implantable device in accordance with another embodiment. In some embodiments of method 700, an implantable device (e.g., implantable device 104) employs a communication component (e.g., communication component 202), an authorization component (e.g., authorization component 204) and a telemetry regulation component (e.g., telemetry regulation component 206) to facilitate minimizing telemetry overuse of the implantable device. Repetitive description of like elements employed in other embodiments described herein is omitted for sake of brevity.

Method 700 can begin in a same or similar manner as methods 500 and 600. For example, at 702, the implantable device connects with an external device (e.g., external device 116). At 704, the implantable device determines whether a downlink packet is received within the defined time window. If a downlink packet is not received, the implantable device considers the external device unauthorized to communicate with the implantable device and method 700 proceeds to block 712 and the implantable device disconnects from the external device (i.e., the implantable device stops communicating with the external device). If a downlink packet is received within the defined time window, at 706, the implantable device analyzes/processes the downlink packet and determines whether the external device is authorized to communicate with the implantable device. In response to a determination at 706 that the external device is authorized to communicate with the implantable device based on analysis of the downlink packet, at 708, the implantable device continues communication with the external device.

However, based on a determination at 706 that the external device is unauthorized to communicate with the implantable device, the implantable device then determines at 710 whether another downlink packet is received from the external device within the defined window of time. In response to a decision at 710 that another downlink packet is not received from the external device, the implantable device disconnects from the external device at 712. In response to a decision at 710 that another downlink packet is received from the external device within the defined window of time, the implantable device further proceeds through decisions 706 and 710 again until the defined window of time has passed.

In addition to disconnecting from the external device, following a determination that the external device is unauthorized to communicate with the implantable device, at 714, the implantable device determines whether a number of failed attempts to authorize external devices during a current time period (e.g., the current calendar day) exceeds a threshold amount. For example, rather than analyzing unauthorized telemetry requests received only from the external device, the implantable device can determine a total number of unauthorized telemetry request received during the current time period, including unauthorized telemetry requests received from the external device and other external devices. In response to a determination at 714 that the number of unauthorized telemetry requests received in the current time period exceeds the threshold amount, method 700 continues to block 720 and the implantable device disables future telemetry with the external device or the external device and other external devices for a defined duration. For example, in one implementation, at 720, the implantable device is configured to prevent the additional communication with the external device for the defined duration but allow additional communication with other external devices. In another implementation, at 720, the implantable device is configured to prevent additional communication with the external device and other external devices for the defined duration. For example, the implantable device can deactivate its transceiver so that no data packets are transmitted or received by the implantable device over the defined duration. In response to a determination at 714 that the number of unauthorized telemetry requests does not exceed the threshold amount, method 700 proceeds to block 716.

At 716, the implantable device determines whether an amount of telemetry performed by the implantable device during a current time period (e.g., a current calendar day), exceeds another threshold amount. In response to a determination that the amount of data usage exceeds the threshold amount, method 700 continues to block 720 wherein the implantable device disables future telemetry with the external device or the external device and other external devices for a defined duration. However, in response to a determination at 716 that the amount of data usage by the implantable device does not exceed the threshold amount, method 700 continues to block 718, wherein the implantable device maintains enablement of telemetry communication according to standard protocol (e.g., BLE protocol).

In an alternative embodiment, at 720, the implantable device can deactivate its receiver but maintain activation of its transmitter. According to this embodiment, the implantable device can continue to transmit non-sensitive or non-critical information and/or to transmit information to trusted devices (e.g., using one-way communications), yet refrain from receiving new connection requests from other devices over the defined duration. Still in another alternative embodiment, at 720, the implantable device can switch to employing a secondary telemetry communication apparatus or protocol (e.g., NFC, inductive communication, or a proprietary telemetry communication protocol) for the defined duration that facilities telemetry communication between the implantable device and one or more authorized external devices.

Figure 8:
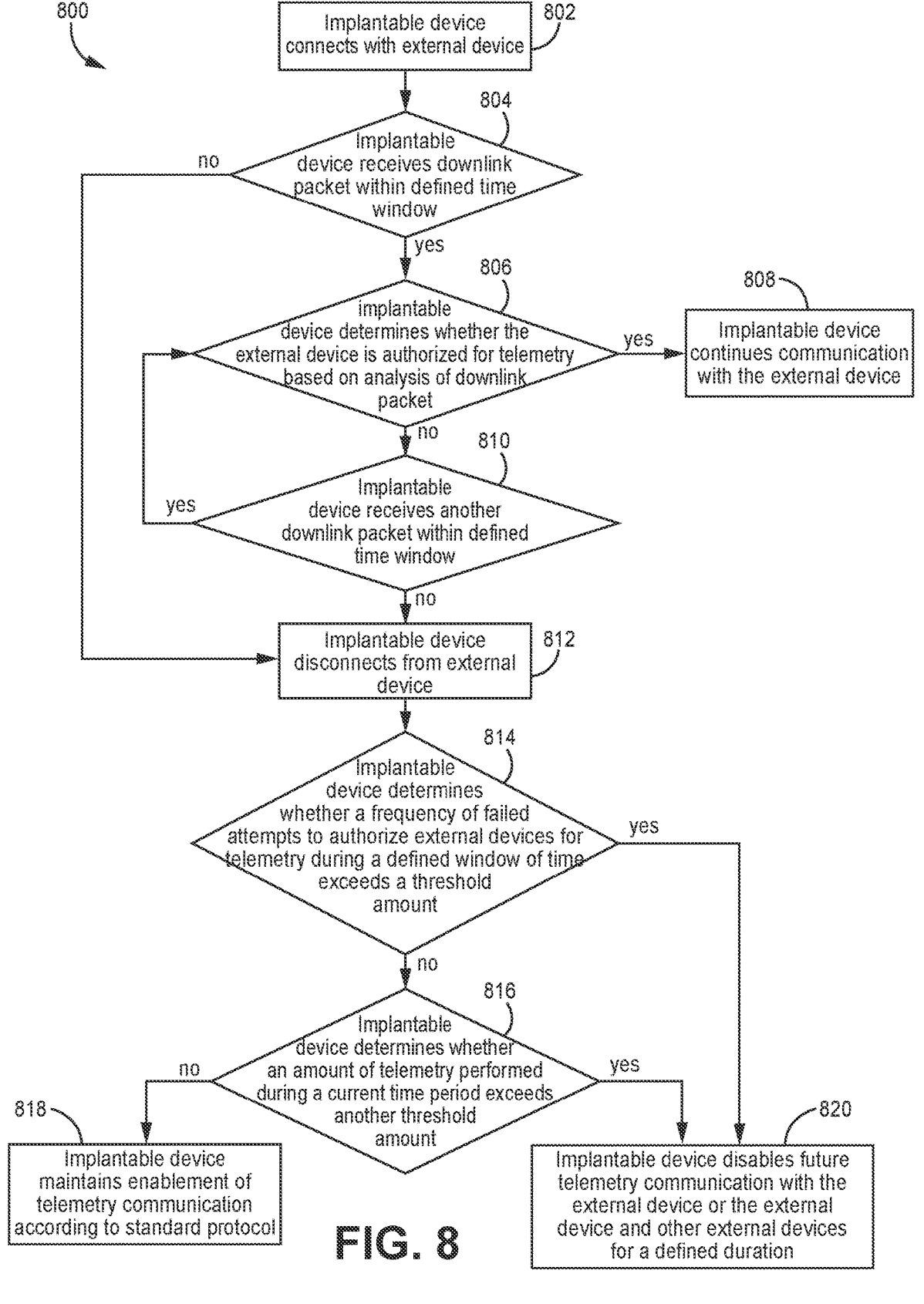

FIG. 8 presents a flow diagram of another example method 800 configured to facilitate telemetry overuse reduction in an implantable device in accordance with another embodiment. In some embodiments of method 800, an implantable device (e.g., implantable device 104) employs a communication component (e.g., communication component 202), an authorization component (e.g., authorization component 204) and a telemetry regulation component (e.g., telemetry regulation component 206) to facilitate minimizing telemetry overuse of the implantable device. Repetitive description of like elements employed in other embodiments described herein is omitted for sake of brevity.

Method 800 can begin in a same or similar manner as methods 500, 600 and 700. For example, at 802, the implantable device connects with an external device (e.g., external device 116). At 804, the implantable device determines whether a downlink packet is received within the defined time window. If a downlink packet is not received, the implantable device considers the external device unauthorized to communicate with the implantable device and method 800 proceeds to block 806 and the implantable device disconnects from the external device (i.e., the implantable device stops communicating with the external device). If a downlink packet is received within the defined time window, at 806, the implantable device analyzes/processes the downlink packet and determines whether the external device is authorized to communicate with the implantable device. In response to a determination at 806 that the external device is authorized to communicate with the implantable device based on analysis of the downlink packet, at 808, the implantable device continues communication with the external device.

However, based on a determination at 806 that the external device is unauthorized to communicate with the implantable device, the implantable device then determines at 810 whether another downlink packet is received from the external device within the defined window of time. In response to a decision at 810 that another downlink packet is not received from the external device, the implantable device disconnects from the external device at 812. In response to a decision at 810 that another downlink packet is received from the external device within the defined window of time, the implantable device further proceeds through decisions 806 and 810 again until the defined window of time has passed.

In addition to disconnecting from the external device, following a determination that the external device is unauthorized to communicate with the implantable device, at 814, the implantable device determines whether a frequency of failed attempts to authorize external devices during a defined window of time exceeds a threshold amount. For example, instances of unusually high amounts of unauthorized telemetry requests received over a short window of time (e.g., one minute, five minutes, thirty minutes, etc.) can correlate to a telemetry overuse scenario. In order to identify and remediate these scenarios, the implantable device can monitor when unauthorized telemetry requests received (e.g., from any device) and monitor durations of time between reception of the respective unauthorized telemetry requests. The implantable device can further implement a threshold requirement with respect to a frequency of unauthorized telemetry requests received in a window of time (e.g., five minutes, 10 minutes, etc). In response to a determination at 814 that the frequency of unauthorized telemetry requests received in a defined window of time exceeds the threshold amount, method 800 continues to block 820 and the implantable device disables future telemetry with the external device or the external device and other external devices for a defined duration. For example, in one implementation, at 820, the implantable device is configured to prevent the additional communication with the external device for the defined duration but allow additional communication with other external devices. In another implementation, at 820, the implantable device is configured to prevent additional communication with the external device and other external devices for the defined duration. For example, the implantable device can deactivate its transceiver so that no data packets are transmitted or received by the implantable device over the defined duration. In response to a determination at 814 that the frequency does not exceed the threshold amount, method 800 proceeds to block 816.

At block 816, the implantable device determines whether an amount of telemetry performed by the implantable device during a current time period (e.g., a current calendar day), exceeds another threshold amount. In response to a determination that the amount of data usage exceeds the threshold amount, method 800 continues to block 820 wherein the implantable device disables future telemetry with the external device and other external devices for a defined duration. However, in response to a determination at 816 that the amount of data usage by the implantable device does not exceed the threshold amount, method 800 continues to block

818, wherein the implantable device maintains enablement of telemetry communication according to standard protocol (e.g., BLE protocol).

In an alternative embodiment, at 820, the implantable device can deactivate its receiver but maintain activation of its transmitter. According to this embodiment, the implantable device can continue to transmit non-sensitive or non-critical information and/or to transmit information to trusted devices (e.g., using one-way communications), yet refrain from receiving new connection requests from other devices over the defined duration. Still in another alternative embodiment, at 820, the implantable device can switch to employing a secondary telemetry communication apparatus or protocol (e.g., NFC, inductive communication, or a proprietary telemetry communication protocol) for the defined duration that facilities telemetry communication between the implantable device and one or more authorized external devices.

FIG. 9 presents a flow diagram of another example method 900 configured to facilitate telemetry overuse reduction in an implantable device in accordance with another embodiment. Method 900 facilitates communicating with an implantable medical device (e.g., implantable device 104) configured to at least one of obtain sensed physiological data associated with a patient and deliver a therapy to the patient. In some embodiments of method 900, an implantable device (e.g., implantable device 104) employs a communication component (e.g., communication component 202), an authorization component (e.g., authorization component 204) and a telemetry regulation component (e.g., telemetry regulation component 206) to facilitate minimizing telemetry overuse of the implantable device. Repetitive description of like elements employed in other embodiments described herein is omitted for sake of brevity.

At 902, an implantable device including a processor (e.g., implantable device 104), establishes a telemetry connection with an external device to communicate data associated with at least one of, physiological data associated with a patient that was sensed by the implantable device, or the therapy data associated with a therapy that was delivered by the implantable device to the patient. For example, the implantable device can receive a request from the external device to establish a telemetry session with the implantable device. The implantable device can then respond to the request, initiate a pairing procedure, and/or initiate an authentication procedure in order to establish a secure telemetry session with the external device. At 904, the implantable device determines whether the external device is authorized to communicate with the implantable device. For example, the implantable device can determine whether the external device is authorized to communicate with the implantable device based on reception of a valid downlink packet from the external devices within a defined window of time. The validity of the downlink packet can be determined based on an ability of the implantable device to decrypt the downlink packet, inclusion of a valid sequence identifier, inclusion of a valid CRC, formatting as a proper command request based on the telemetry protocol employed by the implantable device, and other possible criteria. At 906, the implantable device disables the telemetry connection with the external device and prevents additional telemetry communication with the external device for a defined period of time based in part on a determination that the external device is not authorized to communicate with the implantable device. In another embodiment, the implantable device also prevents additional communication with other external devices for the defined period of time based in part on the determination that the external device is not authorized to communicate with the implantable device. For example, the implantable device can deactivate transmission and/or reception of any data packets for the defined period of time.

FIG. 10 presents a flow diagram of an example method 1000 configured to facilitate telemetry overuse reduction in an implantable device in accordance with another embodiment. Method 1000 facilitates communicating with an implantable medical device (e.g., implantable device 104) configured to obtain sensed physiological data associated with a patient and/or deliver a therapy to the patient. In some embodiments of method 1000, an implantable device (e.g., implantable device 104) employs a communication component (e.g., communication component 202), an authorization component (e.g., authorization component 204) and a telemetry regulation component (e.g., telemetry regulation component 206) to facilitate minimizing telemetry overuse of the implantable device. Repetitive description of like elements employed in other embodiments described herein is omitted for sake of brevity.

At 1002, an implantable device including a processor (e.g., implantable device 104), establishes a telemetry connection with an external device. At 1004, the implantable device determines that the external device is unauthorized to communicate with the implantable device. For example, the implantable device can determine that the external device is unauthorized to communicate with the implantable device based on failure to receive a valid downlink packet from the external devices within a defined window of time following establishment of the telemetry connection. In another example, the implantable device can determine that the external device is unauthorized to communicate with the implantable device based on an inability to decrypt a received downlink packet, inclusion of a invalid sequence identifier in the downlink packet, inclusion of an invalid CRC in the downlink packet, and/reception of an invalid command from the external device.

At 1006, the implantable device disables the telemetry connection with the external device based on the determining that the external device is unauthorized to communicate with the implantable device. For example, the implantable device can stop communicating with the external device and/or abort the pairing procedure. At 1008, based on the determining that the external device is unauthorized to communicate with the implantable device, the implantable device then determines an amount of unauthorized telemetry requests received (e.g., from any external device) by the implantable device within a defined time period (e.g., the current calendar day). The implantable device also determines an amount of telemetry usage by the implantable device within the defined time period. At 1010, the implantable device prevents future telemetry communication with the external device and other external devices based on a determination that the amount of unauthorized telemetry requests exceeds a threshold amount and/or another determination that the amount of telemetry usage exceeds another threshold amount.

FIG. 11 illustrates a flow diagram of another example method 1100 configured to facilitate telemetry overuse reduction in an implantable device in accordance with another embodiment. Method 1000 facilitates communicating with an implantable medical device (e.g., implantable device 104) configured to obtain sensed physiological data associated with a patient and/or deliver a therapy to the patient. In some embodiments of method 1100, an implantable device (e.g., implantable device 104) employs a communication component (e.g., communication component 202), an authorization component (e.g., authorization component 204) and a telemetry regulation component (e.g., telemetry regulation component 206) to facilitate minimizing telemetry overuse of the implantable device. Repetitive description of like elements employed in other embodiments described herein is omitted for sake of brevity.

At 1102, an implantable device including a processor (e.g., implantable device 104), establishes a telemetry connection with an external device. At 1104, the implantable device determines that the external device is unauthorized to communicate with the implantable device (e.g., via the mechanisms described herein). At 1106, the implantable device disables the telemetry connection with the external device based on the determination that the external device is unauthorized to communicate with the implantable device.

At 1108, based on the determination that the external device is unauthorized to communicate with the implantable device, the implantable device determines telemetry regulation parameters, including: an amount of unauthorized telemetry requests received by the implantable device within a defined time period, respective types of the requests, and an amount of telemetry usage by the implantable device within the defined time period. At 1110, the implantable device determines a telemetry regulation score based on the telemetry regulation parameters. For example, the implantable device can employ an algorithm that outputs a score value based on the amount of unauthorized telemetry requests received, weighted values for the types of the respective unauthorized telemetry request (i.e., wherein a type is based on the reason for determining un-authorization), and the amount of telemetry usage thus far within the defined time period. At 1112, the implantable device further disables future telemetry communication with the external device and other external devices for another defined time period based on the telemetry regulation score exceeding a threshold value. In some implementations, the duration of the other defined time period is determined based on the telemetry regulation score. For example, the duration of time can increase as the telemetry regulation score increases.

Figure 12:
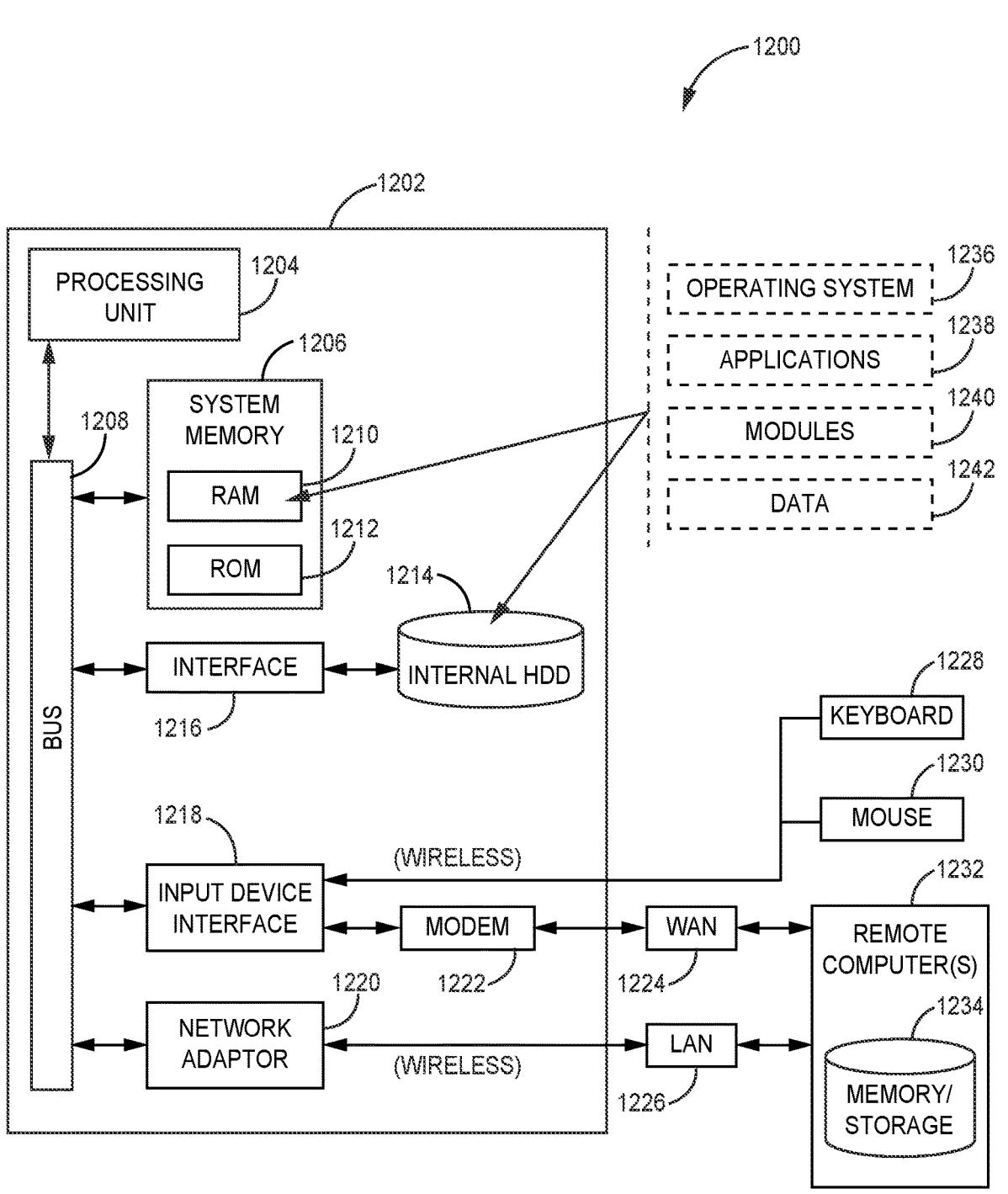
FIG. 12 illustrates a block diagram of an example, non-limiting computer operable to facilitate telemetry overuse reduction in an implantable device in accordance with one or more embodiments described herein.

FIG. 12 illustrates a block diagram of an example, non-limiting computer operable to facilitate telemetry overuse reduction in an implantable device in accordance with one or more embodiments described herein. For example, in some embodiments, the computer can be or be included within implantable device 104 and/or external device 116. Repetitive description of like elements employed in other embodiments described herein is omitted for sake of brevity.

In order to provide additional context for one or more embodiments described herein, FIG. 12 and the following discussion are intended to provide a brief, general description of a suitable computing environment 1200 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 12, example environment 1200 that can be employed to implement one or more embodiments of the embodiments described herein includes computer 1202. Computer 1202 includes processing unit 1204, system memory 1206 and system bus 1208. System bus 1208 couples system components including, but not limited to, system memory 1206 to processing unit 1204. Processing unit 1204 can be any of various commercially available processors. Dual microprocessors and other multiprocessor architectures can also be employed as processing unit 1204.

System bus 1208 can be any of several types of bus structure that can further interconnect to a memory bus (with or without a memory controller), a peripheral bus, and a local bus using any of a variety of commercially available bus architectures. System memory 1206 includes RAM 1210 and ROM 1212. A basic input/output system (BIOS) can be stored in a non-volatile memory such as ROM, erasable programmable read only memory (EPROM), EEPROM, which BIOS contains the basic routines that help to transfer information between elements within computer 1202, such as during startup. RAM 1210 can also include a high-speed RAM such as static RAM for caching data.

Computer 1202 further includes internal hard disk drive (HDD) 1214 (e.g., Enhanced Integrated Drive Electronics (EIDE), Serial Advanced Technology Attachment (SATA)). HDD 1214 can be connected to system bus 1208 by hard disk drive interface 1216. The drives and their associated computer-readable storage media provide nonvolatile storage of data, data structures, computer-executable instructions, and so forth. For computer 1202, the drives and storage media accommodate the storage of any data in a suitable digital format.

A number of program modules can be stored in the drives and RAM 1210, including operating system 1236, one or more application programs 1238, other program modules 1240 and program data 1242. All or portions of the operating system, applications, modules, and/or data can also be cached in RAM 1210. The systems and methods described herein can be implemented utilizing various commercially available operating systems or combinations of operating systems.

A mobile device can enter commands and information into computer 1202 through one or more wireless input devices, e.g., wireless keyboard 1228 and a pointing device, such as wireless mouse 1230. Other input devices (not shown) can include a smart phone, tablet, laptop, wand, wearable device or the like. These and other input devices are often connected to the processing unit 1204 through input device interface 1218 that can be coupled to system bus 1208, but can be connected by other interfaces, such as a parallel port, an IEEE serial port, a game port and/or a universal serial bus (USB) port.

Computer 1202 can operate in a networked environment using logical connections via wired and/or wireless communications to one or more remote computers, such as remote computer(s) 1232. Remote computer(s) 1232 can be a workstation, a server computer, a router, a personal computer, portable computer, microprocessor-based entertainment appliance, a peer device or other common network node, and typically includes many or all of the elements described relative to computer 1202, although, for purposes of brevity, only memory/storage device 1234 is illustrated. The logical connections depicted include wired/wireless connectivity to a local area network (LAN) 1226 and/or larger networks, e.g., WAN 1224, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1202 can be connected to local network through a wired and/or wireless communication network interface or adapter 1220. Adapter 1220 can facilitate wired or wireless communication to LAN 1226, which can also include a wireless access point (AP) connected to the LAN 1226 for communicating with adapter 1220.

When used in a WAN networking environment, computer 1202 can include modem 1222 or can be connected to a communications server on WAN 1224 or has other apparatus for establishing communications over WAN 1224, such as by way of the Internet. Modem 1222, which can be internal or external and a wired or wireless device, can be connected to system bus 1208 via input device interface 1218. In a networked environment, program modules depicted relative to computer 1202 or portions thereof, can be stored in a remote memory/storage device. It will be appreciated that the network connections shown are example and other apparatus of establishing a communications link between the computers can be used.

Computer 1202 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 12 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, $x=(x_1, x_2, x_3, \ldots x_4, x_n)$, to a confidence that the input belongs to a class, that is, $f(x)=confidence$ (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and non-volatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration.

Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A first device comprising:
a housing; and
a processor, within the housing, configured to execute executable components, wherein the executable components comprise:
a communication component configured to establish a wireless communication session with a second device; and
an authorization component configured to determine whether the second device provided authorization for the wireless communication session with the first device, wherein the communication component is further configured to disable the wireless communication session with the second device based on a determination that the second device failed to provide authorization for the wireless communication session with the first device.

2. The first device of claim 1, wherein the communication component is further configured to prevent additional communication with at least the second device based on the determination that the second device failed to provide authorization for the wireless communication session with the first device.

3. The first device of claim 2, wherein the communication component is further configured to prevent additional communication with at least the second device for a period of time.

4. The first device of claim 3, wherein the period of time is a defined period of time.

5. The first device of claim 2, wherein the communication component is further configured to prevent additional communication with other devices based on the determination that the second device failed to provide authorization for the wireless communication session to communicate with the first device.

6. The first device of claim 1, wherein the communication component is configured to establish the wireless communication session with the second device using a Bluetooth Low Energy communication protocol.

7. The first device of claim 1, wherein the authorization component is configured to determine whether the second device provided authorization for the wireless communication session with the first device based on reception of valid authorization information from the second device.

8. The first device of claim 1, wherein the authorization component is configured to determine whether the second device provided authorization for the wireless communication session with the first device based on reception of a packet from the second device within a window of time following reception of a request, from the second device, to establish the wireless communication session.

9. The first device of claim 1, wherein the authorization component is configured to determine whether the second device provided authorization for the wireless communication session with the first device based on reception of a packet from the second device within a window of time following transmission of an acknowledgment message to the second device by the first device, wherein the acknowledgment message indicates the first device has received a request, from the second device, to establish the wireless communication session.

10. The first device of claim 1, wherein the authorization component is further configured to associate the second device with a storage cell that characterizes the second device as unauthorized to communicate with the first device based on the determination that the first device failed to provide authorization for the wireless communication with the first device, and wherein the communication component is configured to reject future requests, received from the second device, to pair with the first device, based on association of the second device with the storage cell.

11. The first device of claim 1, further comprising:
a regulation component configured to determine, based on the determination that the second device failed to provide authorization for the wireless communication with the first device, a number of previous failed attempts to authorize the second device in association with establishing one or more previous wireless communications sessions with the first device, and
wherein the communication component is further configured to disable the wireless communication session with the second device based on the determination that the second device failed to provide authorization for the wireless communication session with the first device and a determination that the number of previous failed attempts exceeds a threshold amount.

12. The first device of claim 11, wherein based on the determination that the second device failed to provide authorization for the wireless communication session with the first device and the determination that the number of previous failed attempts exceeds the threshold amount, the regulation component is further configured to determine an amount of wireless communication conducted by the first device over a period of time, and
wherein the communication component is further configured to disable a connection with the second device and enable additional communication with the second device and other devices based on a determination that the amount of communication fails to exceed the threshold amount.

13. The first device of claim 11, wherein based on the determination that the second device failed to provide authorization for the wireless communication session with the first device and the determination that the number of previous failed attempts exceeds the threshold amount, the regulation component is further configured to determine an amount of communication conducted by the first device over a period of time, and
wherein the communication component is further configured to disable the wireless communication session with the second device and prevent additional communication with the second device and other devices based on a determination that the amount of wireless communication exceeds the threshold amount.

14. The first device of claim 1, further comprising:
a regulation component configured to determine, based on the determination that the second device failed to provide authorization for the wireless communication session with the first device, a number of requests received by the first device from one or more unauthorized devices over a period of time, and
wherein the communication component is further configured to disable the wireless communication session with the second device based on the determination that the second device failed to provide authorization for the wireless communication session with the second device and a determination that the number of requests received by the first device from the one or more unauthorized devices exceeds a threshold amount.

15. The first device of claim 14, wherein the communication component is further configured to prevent additional communication with the second device and other devices based on the determination that the second device failed to provide authorization for the wireless communication session with the second device and the determination that the number of requests received by the first device from the one or more unauthorized devices exceeds the threshold amount, and
wherein the communication component is configured to prevent the additional communication with the second device and the other devices by deactivating a transceiver of the first device for the defined period of time.

16. The first device of claim 1, further comprising:
a regulation component configured to determine, based on the determination that the second device failed to provide authorization for the wireless communication session with the first device, an amount of communication conducted by the first device over a period of time, and
wherein the communication component is further configured to disable a connection with the second device based on the determination that the second device failed to provide authorization for the wireless communication session with the first device and a determination that the amount of communication conducted by the first device over the period of time exceeds a threshold amount.

17. The first device of claim 1, further comprising:
a regulation component configured to determine, based on the determination that the second device failed to provide authorization for the wireless communication session with the first device, a number of requests received by the first device from one or more unauthorized devices over a period of time, and an amount of communication conducted by the first device over the period of time, and wherein the communication component is further configured to disable the wireless communication session with the second device based on the determination that the second device failed to provide authorization for the wireless communication session with the second device, a determination that the number of requests received from the one or more unauthorized devices over the period of time exceeds a threshold amount, and a determination that the amount of the wireless communication session conducted by the first device over the period of time exceeds another threshold amount.

18. A method of communicating by a first device, the method comprising:

receiving, by the first device comprising a processor, a request from a second device to establish a wireless communication session between the second device and the first device;

determining whether the second device provided authorization to establish the wireless communication session with the first device; and deactivating a receiver of the first device based on a determination that the second device failed to provide authorization to establish the wireless communication session with the first device.

19. The method of claim 18, wherein the determining whether the second device provided authorization to establish the wireless communication session with the first device is based on reception of valid authorization information from the second device.

20. The method of claim 18, wherein the determining whether the second device provided authorization to establish the wireless communication session with the first device is based on reception of a defined packet from the second device within a period of time following the request.

* * * * *